United States Patent
Okawara et al.

[11] Patent Number: 5,508,293
[45] Date of Patent: Apr. 16, 1996

[54] PYRIDINECARBOXYIMIDAMIDE COMPOUNDS AND THE USE THEREOF

[75] Inventors: Hideki Okawara, Shibuya; Tatsuo Nakajima, Takasaki; Nobuyuki Ogawa, Takasaki; Tomoko Kashiwabara, Takasaki; Soichiro Kaneta, Takasaki, all of Japan

[73] Assignee: Kirin Beer Kabushiki Kaisha, Tokyo, Japan

[21] Appl. No.: 256,625

[22] PCT Filed: Jan. 28, 1993

[86] PCT No.: PCT/JP93/00103

§ 371 Date: Sep. 27, 1994

§ 102(e) Date: Sep. 27, 1994

[87] PCT Pub. No.: WO93/15057

PCT Pub. Date: Aug. 5, 1993

[30] Foreign Application Priority Data

Jan. 28, 1992 [JP] Japan .................... 4-013342
Mar. 24, 1992 [JP] Japan .................... 4-066221
Dec. 4, 1992 [JP] Japan .................... 4-325760

[51] Int. Cl.⁶ .................... C07D 213/82; A61K 31/44
[52] U.S. Cl. .................... 514/357; 546/300; 546/304; 546/306; 546/309; 546/311; 546/312; 546/315; 546/318; 546/322; 546/326; 546/330
[58] Field of Search .................... 546/300, 306, 546/318, 322, 326, 330, 309, 311, 312, 315, 304; 514/351, 353, 354, 356, 357

[56] References Cited

FOREIGN PATENT DOCUMENTS

| 0388528 | 9/1990 | European Pat. Off. | .......... 546/330 |
| 163061 | 7/1991 | Japan | .......... 546/330 |
| 218343 | 9/1991 | Japan | .......... 546/330 |

OTHER PUBLICATIONS

Kashiwabara, T. et al., Eur. J. Pharmacol., 196(1), 1–7 (1991).
Okada, Y. et al., Br. J. Pharmacol., 104(4), 829–838 (1991).
Ohta, H. et al., Eur. J. Pharmacol., 204(2), 171–177 (1991).
Sakuta, H. et al., Br. J. Pharmacol., 107(4), 1061–1067 (1992).
Ishibashi, T. et al., Naunyn–Schmiedebergs Arch Pharmacol, 346(1), 94–101 (1992).
Jinno, Y. et al., Br. J. Pharmacol, 106(4), 906–909 (1992).
Ogawa, N. et al., J. Cardiovasc. Pharmacol., 20(1), 11–17 (1992).
Ogawa, N. et al., Arch. Int. Parmacodyn Ther., 318, 36–46 (1992).
Kaneta, S. et al., Arch Int. Pharmacodyn Ther., 318, 21–35 (1992).
Yamagishi, T. et al., Naunyn–Schmiedebergs Arch Pharmacol., 346(6), 691–700 (1992).

*Primary Examiner*—C. Warren Ivy
*Assistant Examiner*—Zinna N. Davis
*Attorney, Agent, or Firm*—Oblon, Spivak, McClelland, Maier & Neustadt

[57] ABSTRACT

Disclosed are pyridinecarboximidamides having a vasodilating effect (hypotensive activity or antianginal activity), and acid adduct salts thereof.

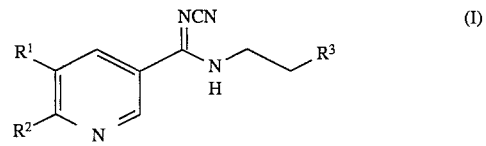

wherein when $R^1$ represents an alkyl, hydroxyalkyl, carboxyl, amino, acylamino, alkylamino, dialkylamino, aralkylamino, alkylsulfonamide, bisalkylsulfonylamino or hydroxyl group, $R^2$ represents a hydrogen atom and $R^3$ represents a nitroxyl, 2-chlorophenyl or phenyl group; and when $R^1$ represents a hydrogen atom, $R^2$ represents an alkyl, hydroxyalkyl, carboxyl, amino, acylamino, alkylamino, dialkylamino, aralkylamino, alkylsulfonamide, bisalkylsulfonylamino or hydroxyl group and $R^3$ represents a nitroxyl, 2-chlorophenyl or phenyl group.

There is also disclosed the use of the compounds represented by the formula (I) for antihypertensive or antianginal purpose.

30 Claims, 2 Drawing Sheets

I-c

I-d (WHEREIN R⁵ REPRESENTS AN ACYLAMINO, ALKYLSULFONAMIDE or BISALKYLSULFONYLAMINO GROUP)

PYRIDINECARBOXYIMIDAMIDE COMPOUNDS AND THE USE THEREOF

This application is a 371 of PCT/JP 93/00103, filed Jan. 28, 1993.

TECHNICAL FIELD

The present invention relates to novel pyridinecarboximidamide compounds having a vasodilating effect.

BACKGROUND ART

Prior to the accomplishment of the present invention, we found that various N-cyano-carboximidamide compounds had a hypotensive activity, a vasodilating effect and the like (as described in Japanese Laid-Open Patent Publications Nos. 163061/1991 and 218343/1991). However, more excellent novel antihypertensive or antianginal agents are strongly demanded when the various conditions of diseases, the quality of life, that is, the support and improvement of patients' daily life, side effects of drugs and the like are taken into consideration.

DISCLOSURE OF THE INVENTION

An object of the present invention is to provide novel compounds having a vasodilating effect, and more specifically compounds having an antihypertensive effect or an antianginal effect. The present invention has been accomplished on the basis of the finding that novel pyridinecarboximidamide compounds have a vasodilating effect.

The pyridinecarboximidamide compounds according to the present invention are represented by the following formula (I):

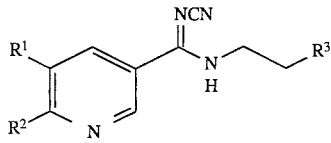

(I)

wherein when $R^1$ represents an alkyl, hydroxyalkyl, carboxyl, amino, acylamino, alkylamino, dialkylamino, aralkylamino, alkylsulfonamide, bisalkylsulfonylamino or hydroxyl $R^2$ represents a hydrogen atom and $R^3$ represents a nitroxyl, 2-chlorophenyl or phenyl group; and when $R^1$ represents a hydrogen atom, represents $R^2$ represents a hydroxyalkyl, carboxyl, amino, acylamino, alkylamino, dialkylamino, aralkylamino, alkylsulfonamide, bisalkylsulfonylamino or hydroxyl group and $R^3$ represents a nitroxyl, 2-chlorophenyl or phenyl group.

The present invention also relates to use of the compounds mentioned above. That is, the antihypertensive agent according to the present invention comprises as an active ingredient a pyridinecarboximidamide represented by formula (I) above or an acid adduct salt thereof, and the antianginal agent comprises as an active ingredient a pyridinecarboximidamide represented by formula (I) above wherein $R^3$ is a nitroxyl group or an acid adduct salt thereof.

The present invention further relates to a method for treatment of hypertension characterized in that a pyridinecarboximidamide represented by formula (I) or an acid adduct salt thereof is administered to a patient who needs the treatment of hypertension and to a method for treatment of angina pectoris characterized in that a pyridinecarboximidamide represented by formula (I) wherein $R^3$ is a nitroxy group or an acid adduct salt thereof is administered to a patient of angina pectoris.

BEST MODE FOR CARRYING OUT THE INVENTION PYRIDINECARBOXIMIDAMIDE COMPOUNDS

As described above, the pyridinecarboximidamide compounds according to the present invention are represented by the following formula (I):

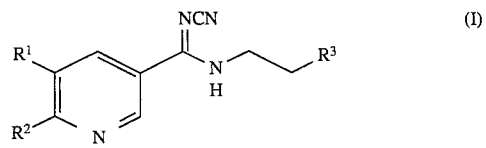

(I)

wherein when $R^1$ represents an alkyl, hydroxyalkyl, carboxyl, amino, acylamino, alkylamino, dialkylamino, aralkylamino, alkylsulfonamide, bisalkylsulfonylamino or hydroxyl group, $R^2$ represents a hydrogen atom and $R^3$ represents a nitroxyl, 2-chlorophenyl or phenyl group; and when $R^1$ represents a hydrogen atom, $R^2$ represents a hydroxyalkyl, carboxyl, amino, acylamino, alkylamino, dialkylamino, aralkylamino, alkylsulfonamide, bisalkylsulfonylamino or hydroxyl group and $R^3$ represents a nitroxyl, 2-chlorophenyl or phenyl group.

Figure 1:
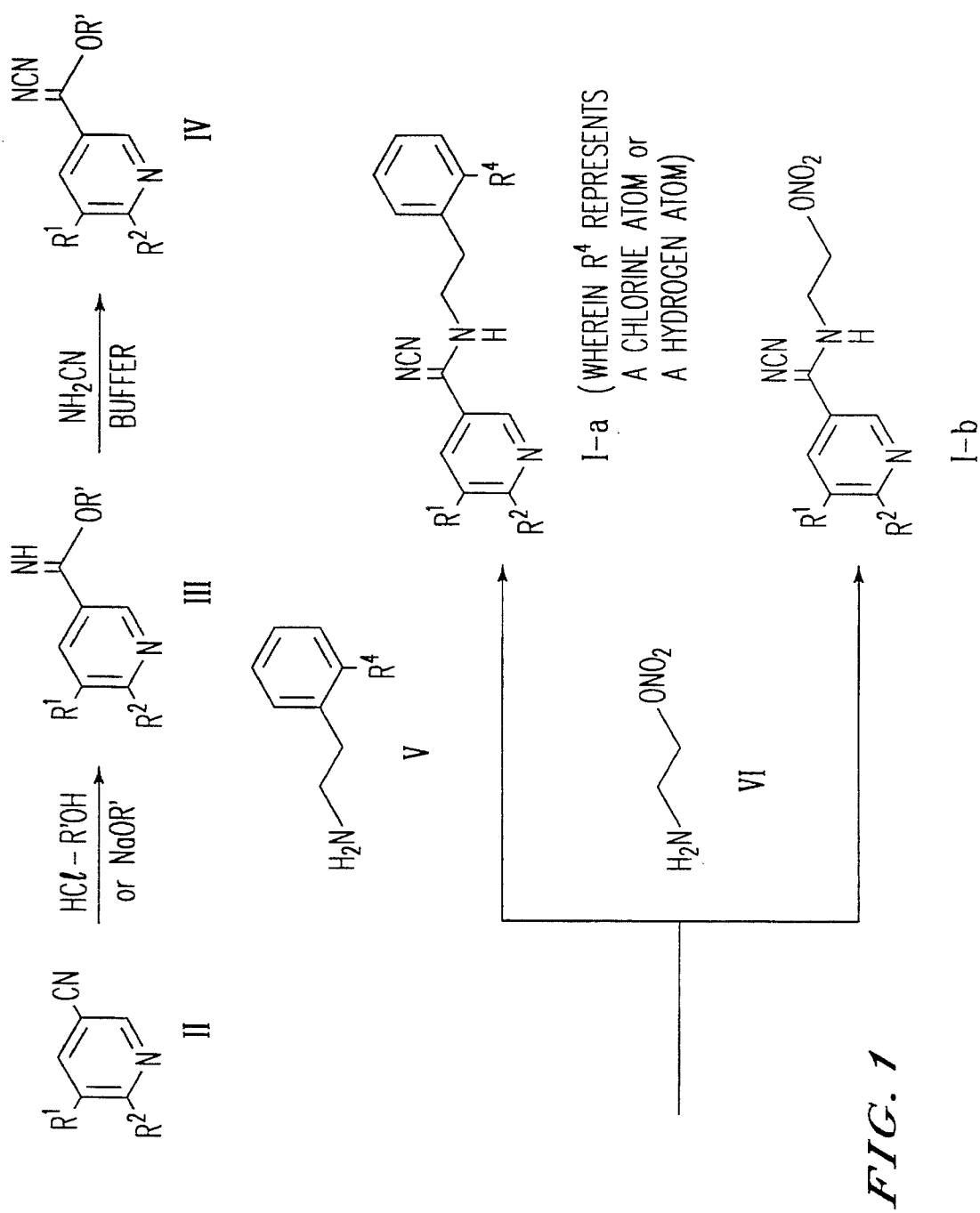
FIG. 1 is a reaction scheme for producing the compound of the present invention represented by the formula (I) and illustrates the production of the N-cyano-pyridinecarboximidamide compound represented by the formula (I) in which $R^1$ represents an alkyl group, a hydroxyalkyl group, a carboxyl group, an amino group, an alkylamino group, a dialkylamino group, an aralkylamino group or a hydroxyl group, and $R^2$ represents a hydrogen atom; or $R^1$ represents a hydrogen atom, and $R^2$ represents an amino group or a dialkylamino group, and an acid adduct salt thereof.

The compounds of the present invention in which $R^3$ is a 2-chlorophenyl or phenyl group in formula (I) are represented by formula (I-a) and the compounds of the present invention in which $R^3$ is a nitroxyl group in formula (I) are represented by formula (I-b) (FIG. 1).

In $R^1$ and $R^2$ in formulae (I), (I-a) and (I-b), preferably, the alkyl group has 1 to 5 carbon atoms, alkyl of the hydroxyalkyl group has 1 to 5 carbon atoms, acyl of the acylamino group is acetyl, propionyl or benzoyl, alkyl of the alkylamino group has 1 to 5 carbon atoms, alkyl of the dialkylamino group has 1 to 5 carbon atoms, the aralkylamino group is benzylamino, alkyl of the alkylsulfonamide group has 1 to 5 carbon atoms, and alkyl of the bisalkylsulfonylamino group has 1 to 5 carbon atoms.

The compounds of the present invention possess a basic nitrogen atom, so that they can form acid adduct salts. Acids which can be used for the formation of the acid adduct salts include, for instance, inorganic acids such as hydrochloric acid, sulfuric acid, nitric acid and phosphoric acid, and organic acids such as acetic acid, propionic acid, maleic acid, oleic acid, palmitic acid, citric acid, succinic acid, tartaric acid, fumaric acid, glutamic acid, pantothenic acid, methanesulfonic acid, toluenesulfonic acid and laurylsulfonic acid. It is needless to say that pharmaceutically acceptable acids should be used for the formation of acid adduct salts which will be used as medicines.

As the representative examples of the pyridinecarboximidamide compounds according to the present invention represented by the formula (I), the following compounds are mentioned:

(1) In the case where $R^3$ is a 2-chlorophenyl or phenyl group:

| Compound No. | Name of Compound |
|---|---|
| 1) | N-cyano-N'-[2-(2-chlorophenyl)ethyl]-5-methyl-3-pyridinecarboximidamide |
| 2) | N-cyano-N'-[2-(2-chlorophenyl)ethyl]-5-ethyl-3-pyridinecarboximidamide |
| 3) | N-cyano-N'-[2-(2-chlorophenyl)ethyl]-5-hydroxymethyl-3-pyridinecarboximidamide |
| 4) | 5-carboxy-N-cyano-N'-[2-(2-chlorophenyl)ethyl]-3-pyridinecarboximidamide |
| 5) | 6-amino-N-cyano-N'-[2-(2-chlorophenyl)ethyl]-3-pyridinecarboximidamide (N-cyano-N'-[2-(2-chlorophenyl)ethyl]-5-(2-aminopyridine)carboximidamide) |
| 6) | 5-amino-N-cyano-N'-[2-(2-chlorophenyl)ethyl]-3-pyridinecarboximidamide (N-cyano-N'-[2-(2-chlorophenyl)ethyl]-5-(3-aminopyridine)carboximidamide) |
| 7) | 5-acetamide-N-cyano-N'-[2-(2-chlorophenyl)ethyl]-3-pyridinecarboximidamide (N-cyano-N'-[2-(2-chlorophenyl)ethyl]-5-[3-(N-acetylamino)pyridine]carboximidamide) |
| 8) | 5-benzamide-N-cyano-N'-[2-(2-chlorophenyl)ethyl]-3-pyridinecarboximidamide |
| 9) | N-cyano-N'-[2-(2-chlorophenyl)ethyl]-5-dimethylamino-3-pyridinecarboximidamide |
| 10) | N-cyano-N'-[2-(2-chlorophenyl)ethyl]-5-ethylamino-3-pyridinecarboximidamide |
| 11) | N-cyano-N'-[2-(2-chlorophenyl)ethyl]-5-isopropylamino-3-pyridinecarboximidamide |
| 12) | 5-n-butylamino-N-cyano-N'-[2-(2-chlorophenyl)ethyl]-3-pyridinecarboximidamide |
| 13) | 5-benzylamino-N-cyano-N'-[2-(2-chlorophenyl)ethyl]-3-pyridinecarboximidamide |
| 14) | N-cyano-N'-[2-(2-chlorophenyl)ethyl]-5-methanesulfonamide-3-pyridinecarboximidamide (N-cyano-N'-[2-(2-chlorophenyl)ethyl]-5-[3-(N-methanesulfonylamino)pyridine]-carboximidamide) |
| 15) | N-cyano-N'-[2-(2-chlorophenyl)ethyl]-5-bis-methanesulfonylamino-3-pyridinecarboximidamide (N-cyano-N'-[2-(2-chlorophenyl)ethyl]-5-[3-(N,N-bismethanesulfonylamino)pyridine]-carboximidamide) |
| 16) | 5-amino-N-cyano-N'-(2-phenethyl)-3-pyridinecarboximidamide |
| 17) | N-cyano-N'-[2-(2-chlorophenyl)ethyl]-5-hydroxy-3-pyridinecarboximidamide |

(2) In the case where $R^3$ is a nitroxy group:

| Compound No. | Name of Compound |
|---|---|
| 18) | 5-amino-N-cyano-N'-(2-nitroxyethyl)-3-pyridinecarboximidamide (N-cyano-N'-(2-nitroxyethyl)-5-(3-aminopyridine)carboximidamide) |
| 19) | N-cyano-5-ethylamino-N'-(2-nitroxyethyl)-3-pyridinecarboximidamide (N-cyano-N'-(2-nitroxyethyl)-5-[3-(N-ethylaminopyridine)carboximidamide) |
| 20) | 6-amino-N-cyano-N'-(2-nitroxyethyl)-3-pyridinecarboximidamide (N-cyano-N'-(2-nitroxyethyl)-5-(2-aminopyridine)carboximidamide) |
| 21) | N-cyano-6-diethylamino-N'-(2-nitroxyethyl)-3-pyridinecarboximidamide (N-cyano-N'-(2-nitroxyethyl)-5-[2-(N,N-diethylamino)pyridine]carboximidamide) |
| 22) | 5-n-butylamino-N-cyano-N'-(2-nitroxyethyl)-3-pyridinecarboximidamide (N-cyano-N'-(2-nitroxyethyl)-5-[3-(N-n-butylamino)pyridine]carboximidamide) |
| 23) | N-cyano-N'-(2-nitroxyethyl)-5-isopropylamino-3-pyridinecarboximidamide (N-cyano-N'-(2-nitroxyethyl)-5-[3-(N-isopropylamino)pyridine]carboximidamide) |
| 24) | 5-acetylamino-N-cyano-N'-(2-nitroxyethyl)-3-pyridinecarboximidamide (N-cyano-N'-(2-nitroxyethyl)-5-[3-(N-acetylamino)pyridine]carboximidamide) |

Process for Preparing Pyridinecarboximidamide Compounds

The pyridinecarboximidamide compounds according to the present invention can be prepared by any method suitable for the purpose, and, for instance, the following methods may be taken for the preparation of the compounds.

A) Preparation of N-cyano-pyridinecarboximidamide compounds represented by the formula (I) wherein $R^1$ is an alkyl, hydroxyalkyl, carboxyl, amino, alkylamino, dialkylamino, aralkylamino or hydroxyl group and $R^2$ is a hydrogen atom, or $R^1$ is a hydrogen atom and $R^2$ is an amino or dialkylamino group, and acid adduct salts thereof:

Among the compounds of the present invention represented by the formula (I), those pyridinecarboximidamide compounds in which $R^1$ is an alkyl, hydroxyalkyl, carboxyl, amino, alkylamino, dialkylamino, aralkylamino or hydroxyl group and $R^2$ is a hydrogen atom, or in which $R^1$ is a hydrogen atom and $R^2$ is an amino or dialkylamino group can be prepared, as shown in FIG. 1, by leading cyanopyridine (II) having the above-described $R^1$ and $R^2$ of the formula (I) to N-cyano-pyridinecarboximidate (IV) via pyridinecarboximidate (III), and then reacting the N-cyanopyridinecarboximidate (IV) with an amine (V) or (VI). It is noted that a pyridinecarboximidamide compound whose $R^1$ is a carboxyl group can be obtained by using cyanopyridine (II) whose $R^1$ is a methoxycarbonyl group as the starting compound, leading it to a pyridinecarboximidamide compound via pyridinecarboximidate (III) and N-cyano-pyridinecarboximidate (IV), and eliminating the methyl group therefrom. The explanation will be given below in order.

1) Cyanopyridine (II)

As mentioned above, among the compounds of the present invention represented by the formula (I), those pyridinecarboximidamide compounds in which $R^1$ is an alkyl, hydroxyalkyl, carboxyl, amino, alkylamino, dialkylamino, aralkylamino or hydroxyl group and $R^2$ is a hydrogen atom, or in which $R^1$ is a hydrogen atom and $R^2$ is an amino or dialkylamino group can be synthesized, as shown in FIG. 1, from cyanopyridine (II) having the above-mentioned $R^1$ and $R^2$. The cyanopyridine may be either a known compound or a compound prepared by a known method as shown in, for instance, Journal of Medicinal Chemistry 10, 149–154 (1967), Journal of Heterocyclic Chemistry 11, 397–399 (1974), Heterocycles 22, 117–124 (1984) or the like.

2)- Preparation of Pyridinecarboximidate (III)

As one of the methods for preparing pyridinecarboximidate (III) from the cyanopyridine (II), the Pinner's method can be mentioned. Namely, by treating the cyanopyridine (II) with hydrogen chloride gas in an alcohol, alkyl pyridinecarboximidate corresponding to the alcohol employed can be obtained. Alcohols which can be used in the above reaction include, for example, methanol, ethanol, 1-propanol, 2-propanol, 1-butanol, isobutyl alcohol and t-butyl alcohol. The alcohol can be used also as a reaction solvent. Furthermore, it can be used simply as a reagent in the coexistence of other solvents. When the alcohol is used also as a reaction solvent, the amount of the alcohol is usually in the range of 50 to 200 moles per 1 mole of the cyanopyridine. When the alcohol is used in the presence of other solvents, the preferable amount of the alcohol is 1 to 5 moles per 1 mole of the cyanopyridine. Solvents which can be used in this reaction include, for example, aprotic solvents such as hexane, benzene, toluene, diethyl ether and petroleum ether. The reaction temperature is preferably in the range of −10° to 50° C., particularly from 0° C. to room temperature.

The reaction can be completed, in general, in 1 to 24 hours under the above-described reaction conditions.

The pyridinecarboximidate (III) obtained by above reaction is in the form of a hydrochloric acid salt. This salt can be supplied to the succeeding reaction either as it is or after the neutralization of hydrochloric acid with an alkali. Moreover, it is possible to subject the pyridinecarboximidate (III) or its hydrochloric acid salt to isolation and purification. In this case, any one of the purification methods conventionally known in the field of organic chemistry, such as crystallization, distillation and column chromatography using silica gel as a support, can be taken.

The pyridinecarboximidate (III) can also be prepared by another method. Namely, the pyridinecarboximidate (III) can be obtained by treating the cyanopyridine (II) with a catalytic amount of a metal alcoholate in an alcohol. Sodium alcoholate and potassium alcoholate can be mentioned as examples of the metal alcoholate. Alcohols which can be used in this reaction and the amount thereof are the same as those described in the preparation process according to the Pinner's method. Further, this reaction can be carried out also in the coexistence of other solvents as described above, and solvents which can be used in this reaction are the same as those mentioned above. The reaction temperature is preferably in the range of the freezing point of the solvent used to 30° C., particularly from 0° to 10° C. The reaction can be completed, in general, in 12 to 24 hours.

The isolation and purification of the pyridinecarboximidate obtained by this reaction can be conducted by the same method as is shown in the above.

3) Conversion into N-cyano-pyridinecarboximidate (IV)

The above-obtained pyridinecarboximidate (III) or its hydrochloric acid salt is converted into N-cyano-pyridinecarboximidate (IV) when it is reacted with cyanamide.

The amount of the cyanamide used is preferably 1 mole or more, particularly 2 to 3 moles per 1 mole of the pyridinecarboximidate (III). This reaction depends on the pH of the reaction solution, and the optimum pH range is preferably from 6.0 to 8.0, more preferably from 6.5 to 7.5. In order to keep the pH in the above optimum range, it is suitable that the reaction is carried out in a phosphoric acid buffer solution, or with the addition of a base such as sodium carbonate when a hydrochloric acid salt is used as a substrate. Moreover, this reaction can be carried out also in the coexistence of other solvents. Solvents which can be used in the reaction include acetonitrile, dioxane, tetrahydrofuran and DMF. The reaction temperature is preferably in the range of 0° to 50° C., and around room temperature is particularly preferred.

The reaction can be completed in 5 to 30 hours under the aforementioned reaction conditions.

The N-cyano-pyridinecarboximidate (IV) thus obtained can be isolated and purified by the same method as is described above, such as crystallization, distillation or column chromatography using silica gel as a support.

4) Preparation of N-cyano-pyridinecarboximidamide

N-Cyano-pyridinecarboximidamides represented by the formulas (I-a) and (I-b) can be obtained by reacting the above-obtained N-cyano-pyridinecarboximidate (IV) with an amine (V) and (VI), respectively. The suitable amount of the amine used is 1 mole or more, preferably from 1 to 2 moles per 1 mole of the N-cyano-pyridinecarboximidate (IV). This reaction is usually carried out in a solvent. Solvents which can be used in the reaction include, for example, organic solvents such as methanol, ethanol, dichloromethane, chloroform, carbon tetrachloride, dioxane and tetrahydrofuran, and water. The reaction temperature is in the range of 0° C. to the boiling point of the solvent used, and around room temperature is particularly preferred. This reaction can be completed, in general, in 2 to 24 hours under the above-described reaction conditions.

The isolation and purification of the N-cyano-pyridinecarboximidamides represented by the formula (I) ((I-a) and (I-b)) from the reaction solution obtained by the above reaction can be conducted by the same method as is mentioned in the item of the isolation and purification of the pyridinecarboximidate (III).

The N-cyano-pyridinecarboximidamides ((I-a) and (Ib)) thus obtained can be made into acid adduct salts by reacting them with an acid. Acids which can be used are the same as above.

Figure 2:
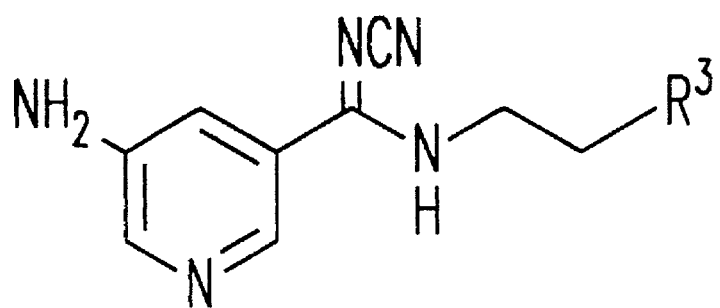
FIG. 2 is a reaction scheme for the production of the compound of the present invention represented by the formula (I) and illustrates the production of the N-ecyano-pyridinecarboximidamide compound in which $R^1$ represents an acylamino group, an alkylsulfonamide group or bisalkylsulfonylamino group, and an acid adduct salt thereof.
Figure 2:
Figure 2:
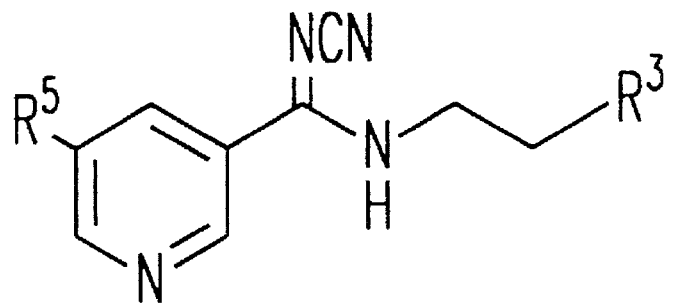

B) Preparation of N-cyano-pyridinecarboximidamide compounds represented by the formula (I) wherein $R^1$ is an acylamino, alkylsulfonamide or bisalkylsulfonylamino group, and acid adduct salts thereof:

Among the compounds of the present invention represented by the formula (I), N-cyano-pyridinecarboximidamide in which $R^1$ is an acylamino, alkylsulfonamide or bisalkylsulfonylamino group can be prepared, as shown in FIG. 2, by using as the starting compound the N-cyano-pyridinecarboximidamide (I-c) having an amino group as $R^1$ in the formula (I) obtained by the above-described reaction, and subjecting the amino group which is bonded to pyridine to acylation, alkylsulfonylation or bisalkylsulfonylation.

This preparation method will be more specifically explained below.

The captioned compound represented by the formula (I-d) can be prepared by subjecting the amino group in the compound (I-c) to N-acylation or N-alkylsulfonylation. The N-acylation or N-alkylsulfonylation can be carried out by any one of various conventional manners, and, for instance, the following manner may be taken for the purpose.

The compound (I-d) can be obtained by reacting the amino group in the compound (I-c) with an acylating or sulfonylating agent such as an acid halide, an acid anhydride or an active ester; or by reacting the amino group with carboxylic acid with the addition of a condensing agent such as 1,3-dichlorohexylcarbodiimide (DCC) or 1-ethyl-3-(3'-diethylaminopropyl)-carbodiimide (WSCI). In the case where an acylating agent is used, the suitable amount of the acylating agent is 1 mole or more, preferably from 1 to 2 moles per 1 mole of the starting compound (I-c). This reaction is usually carried out in a solvent. Solvents which can be used in the reaction include, for instance, organic solvents such as pyridine, N,N-dimethylformamide, dichloromethane, chloroform, acetonitrile and tetrahydrofuran. It is desirable to conduct the reaction in the presence of an organic base such as pyridine or triethylamine, or an inorganic base such as potassium carbonate or sodium hydrogencarbonate. The reaction temperature is in the range of 0° C. to the boiling point of the solvent used, and around room temperature is particularly preferred. In the case where a condensing agent is used, it is suitable to conduct the reaction by using carboxylic acid and the condensing agent each in an amount of 1 mole or more per 1 mole of the starting compound (I-c), preferably each in an amount equimolar to the amount of the starting compound. When an additive such as N-hydroxysuccinimide or N-hydroxybenzotriazole is used in this reaction, the reaction proceeds promptly and the yield also increases. This reaction is usually carried out in a solvent. Solvents which can be used in the reaction include, for instance, organic solvents such as N,N-dimethylformamide, acetonitrile and tetrahydrofuran. It is possible to conduct the reaction in water when WSCI is used. The reaction temperature is in the range of 0° C. to the boiling point of the solvent used, and around room temperature is particularly preferred.

These reactions can be completed, in general, in 2 to 24 hours under the above-described two reaction conditions.

The isolation and purification of the pyridine-carboximidamide represented by the formula (I-d) from the reaction solution obtained by the above reaction can be conducted by the same method as is described in the item of the isolation and purification of the pyridinecarboximidate represented by the formula (III).

The N-cyano-pyridinecarboximidamide (I-d) thus prepared can be made into an acid adduct salt by reacting it with an acid. Acids which can be used in the reaction are the same as those described in the above.

Use of Pyridinecarboximidamide Compounds (1) In the case where $R^3$ in the formula (I) is a 2-chlorophenyl or phenyl group:

The pyridinecarboximidamide compounds according to the present invention have, as described before, a hypotensive activity. They are therefore useful as antihypertensive agents.

The pyridinecarboximidamide compounds of the present invention can be administered, as antihypertensive agents, orally, parenterally (intramuscularly, subcutaneously, intravenously, percutaneously), or in the form of a sublingual tablet or a suppository.

It is needless to say that the dose and the administration manner of the pyridinecarboximidamide compound of the present invention vary depending on the state of a patient such as sex and sensitivity, the time for administration, drugs to be used in combination, and the condition of a patient or a disease. In addition, the optimum dose and the frequency of the administration under a certain condition should be determined by a specialist on the basis of the above-described guideline and the results of an optimum dose determining test. In general the dose per adult individual is from about 0.1 to 200 mg, preferably from about 0.3 to 100 mg, more preferably from 0.5 to 50 mg.

In the case of oral administration, the compound of the present invention is administered in the form of tablets, granules, powders or capsules. In the case of parenteral administration, it is administered in the form of injections or suspensions. Upon producing these pharmaceutical preparations, excipients, binding agents, disintegrating agents, lubricants, stabilizers and the like may be added.

Examples of the excipients include lactose, starch, crystalline cellulose, mannitol, maltose, calcium hydrogen phosphate, light anhydrous silicic acid and calcium carbonate. Examples of the binding agents include starch, polyvinylpyrrolidone, hydroxypropylcellulose, ethylcellulose, carboxymethylcellulose and gum arabic. Examples of the disintegrating agents include starch and carboxymethylcellulose. Examples of the lubricants include magnesium stearate, talc and hardened oil. Examples of the stabilizing agents include lactose, mannitol, maltose, Polysorbates and polyoxyethylene hardened castor oil.

Pharmaceutical preparations in the forms of tablets, granules, capsules, injections and the like can be produced by using the above ingredients.

(2) In the case where $R^3$ in the formula (I) is a nitroxyl group:

As mentioned previously, the pyridinecarboximidamide compounds according to the present invention have a vasodilating effect, more specifically a hypotensive activity or an antianginal effect. For this reason, they are useful as antihypertensive or antianginal agents.

The pyridinecarboximidamide compounds according to the present invention can be administered, as antihypertensive or as antianginal agents, orally, parenterally (intramuscularly, subcutaneously, intravenously, percutaneously), or in the form of a sublingual tablet or a suppository.

It is needless to say that the dose and the administration manner of the pyridinecarboximidamide compound of the present invention vary depending on the state of a patient such as sex and sensitivity, the time for administration, drugs to be used in combination, and the condition of a patient or a disease. In addition, the optimum dose and the frequency of the administration under a certain condition should be determined by a specialist on the basis of the above-described guideline and the results of an optimum dose determining test. In general, however, the dose per adult individual is from about 0.1 to 200 mg, preferably from about 0.5 to 100 mg, more preferably from 0.5 to 50 mg.

In the case of oral administration, the compound of the present invention is administered in the form of tablets, granules, powders or capsules. In the case of parenteral administration, it is administered in the form of injections or suspensions. Upon producing these pharmaceutical preparations, excipients, binding agents, disintegrating agents, lubricants and the like can be added.

Examples of the excipients include lactose, starch, crystalline cellulose, mannitol, maltose, calcium hydrogen phosphate, light anhydrous silicic acid and calcium carbonate. Examples of the binding agents include starch, polyvinylpyrrolidone, hydroxypropylcellulose, ethylcellulose, carboxymethylcellulose and gum arabic. Examples of the disintegrating agents include starch and carboxymethylcellulose. Examples of the lubricants include magnesium stearate, talc and hardened oil. Examples of the stabilizing agents include lactose, mannitol, maltose, Polysorbates and polyoxyethylene hardened castor oil.

Pharmaceutical preparations in the forms of tablets, granules, capsules, injections and the like can be produced by using the above ingredients.

As described above, pyridinecarboximidamide compounds according to the present invention are novel compounds having a potent vasodilating effect, more specifically an antihypertensive effect or an antianginal effect. As demonstrated in the Experimental Examples described below, the antihypertensive activity of 5-amino-N-cyano-N'-[2-(2-chlorophenyl)ethyl]-3-pyridinecarboximidamide was particularly determined with the passage of time, and, as a result, it was found that the activity was extremely potent and sustainable. The antihypertensive activity or coronary vasodilating effect of 5-amino-N-cyano-N'-(2-nitroxyethyl)-3-pyridinecarboximidamide was also determined with the passage of time, and it was found to be remarkably potent and sustainable. It can be said that such advantageous properties of the compounds are unexpected ones for the inventors of the present invention.

EXPERIMENTAL EXAMPLES

The present invention is further described in detail with reference to pharmacological tests and examples below, but it should not be construed that the invention is limited thereto.

(1) When $R^3$ in the formula (I) represents a 2-chlorophenyl group or a phenyl group: Pharmacological Test 1: Antihypertensive activities on spontaneously hypertensive rat (intravenously)

Antihypertensive activities of the compounds of the present invention were observed with male spontaneously hypertensive rats (SHR).

Animals were anesthetized with urethane: α-chloralose. A cannula was inserted into the carotid artery for measuring the mean blood pressure via a pressure transducer. A test compound was cumulatively administered through the cannula inserted into the femoral vein with an interval of 30 minutes. Variation of blood pressure was determined as the percentage change in the blood pressure before administration of the test compound, and the $ED_{20}$ (the dose which lowered the blood pressure by 20%) was calculated from a dose-response curve.

Results

The $ED_{20}$ values of the representative compounds among the compounds of the present invention are shown in Table 1.

TABLE 1

| Compound No. | $ED_{20}$ (μg/kg, i.v.) |
|---|---|
| 1 | 17.1 |
| 2 | 7.0 |
| 3 | 8.7 |

TABLE 1-continued

| Compound No. | $ED_{20}$ (μg/kg, i.v.) |
|---|---|
| 5 | 33.3 |
| 6 | 4.6 |
| 7 | 12.3 |
| 10 | 7.9 |
| 16 | 28.0 |

Pharmacological Test 2: Antihypertensive activity of 5-amino-N-cyano-N'-[2-(2-chlorophenyl)ethyl]-3-pyridinecarboximidamide (N-cyano-N'-[2-(2-chlorophenyl)ethyl]-5-(3-aminopyridine)carboximidamide; Compound No. 6) on beagles Antihypertensive activities of 5-amino-N-cyano-N'-[2-(2-chlorophenyl)ethyl]-3-pyridinecarboximidamide (N-cyano-N'-[2-(2-chlorophenyl)ethyl]-5-(3aminopyridine)carboximidamide; Compound No. 6) according to the present invention was assessed by comparison with those of N-cyano-N'-[2-(2-chlorophenyl)ethyl]-3-pyridinecarboximidamide which is thought to be a wellknown compound most similar to the compound of the present invention (see Japanese Patent Laid-Open Publication No. 163061/1991).

Experiments were carried out with beagles (body weight, 9.2–10.4 kg) under anesthetization by intravenous administering 30 mg/kg of pentobarbital sodium. A cannula was inserted into the right femoral artery for measuring blood pressure. The test compound was administered through the cannula inserted into the right femoral artery.

Results

Dose-dependent decrease in blood pressure was observed by intravenously administering 3–30 μg/kg of 5-amino-N-cyano-N'-[2-(2-chlorophenyl)ethyl]-3-pyridinecarboximidamide. The duration of the antihypertensive action lasted 10, 45 and 60 min. at the dose of 3, 10, and 30 μg/kg, respectively. While the decrease in blood pressure was observed on the administration of 10 and 30 μg/kg of N-cyano-N'-[2-(2-chlorophenyl)ethyl]-3-pyridinecarboximidamide, the decrease in blood pressure induced by both doses were recovered within 10 minutes after administration (as shown in Table 2).

TABLE 2

Antihypertensive effects of 5-amino-N-cyano-N'-[2-(2-chlorophenyl)ethyl]-3-pyridinecarboximidamide administered intravenously

| | Antihypertensive activity (%) | | | | | |
|---|---|---|---|---|---|---|
| | 5-Amino-N-cyano-N'-[2-(2-chlorophenyl)ethyl]-3-pyridinecarboxyimidamide Dose (μg/kg) | | | N-Cyano-N'-[2-(2-chlorophenyl)ethyl]-3-pyridinecarboximidamide Dose (μg/kg) | | |
| Time after dosage (min) | 3 | 10 | 30 | 3 | 10 | 30 |
| 0 | 0.0 | 0.0 | 0.0 | 0.0 | 0.0 | 0.0 |
| 1 | −3.9 | −16.0 | −29.3 | 0.0 | −23.4 | −41.7 |
| 2 | −12.8 | −22.7 | −40.0 | 1.9 | −17.7 | −39.8 |
| 3 | −10.3 | −26.7 | −42.7 | 1.9 | −13.1 | −33.3 |
| 5 | −6.4 | −26.7 | −46.7 | | −4.7 | −16.7 |
| 7.5 | −3.9 | −26.7 | −44.0 | | | −2.8 |
| 10 | −3.9 | −26.7 | −42.7 | | | −0.9 |
| 15 | | −20.0 | −40.0 | | | |
| 20 | | −16.0 | −36.0 | | | |
| 30 | | −13.3 | −33.3 | | | |

TABLE 2-continued

Antihypertensive effects of 5-amino-N-cyano-N'-[2-(2-chlorophenyl)ethyl]-3-pyridinecarboximidamide administered intravenously

| Time after dosage (min) | Antihypertensive activity (%) | | | | | |
|---|---|---|---|---|---|---|
| | 5-Amino-N-cyano-N'-[2-(2-chlorophenyl)ethyl]-3-pyridinecarboxyimidamide Dose (μg/kg) | | | N-Cyano-N'-[2-(2-chlorophenyl)ethyl]-3-pyridinecarboximidamide Dose (μg/kg) | | |
| | 3 | 10 | 30 | 3 | 10 | 30 |
| 45 | | | −6.7 | | | −24.0 |
| 60 | | | | | | −16.0 |

Pharmacological Test 3: Antihypertensive activities of 5-amino-N-cyano-N'-[2-(2-chlorophenyl)ethyl]-3-pyridinecarboximidamide (N-cyano-N'-[2-(2-chlorophenyl)ethyl]-5-(3-aminopyridine)carboximidamide) on renal hypertensive beagles Beagles (body weight, 9.0–11.0 kg) were anesthetized with 30 mg/kg of pentobarbital sodium intravenously. The left renal artery was carefully exposed through a flank incision, and wound with two silk sutures and ligated together with a 18G needle (external diameter; 1.2 mm) at two positions with the distance of 5 mm. A polyethylene tube for the measurement of blood pressure (IMG, PE-100) was inserted into the femoral artery, and the other terminal of the tube was exteriorized at the back of the neck. The polyethylene tube was filled with physiological saline containing 500 U/ml of heparin and sealed with a steel wire plug except on the measurement of the blood pressure. Antibiotics (penicilline and streptomycin, manufactured by Meiji Seika) were administered intramuscularly for three days after operation to prevent infections.

Beagles exhibiting an average blood pressure exceeding 120 mmHg after a month of the operation were subjected to the experiment as 2-kidney-1-clipped renal hypertensive dogs.

After 5-amino-N-cyano-N'-[2-(2-chlorophenyl)ethyl]-3-pyridinecarboximidamide was put into a No. 3 gelatin capsule, a gap was filled with lactose (100 mesh). The capsule was administered orally, and blood pressure was measured for 24 hours after administering the drug. Measurement was carried out without anesthetization under suspension with sling sheet. Blood pressure was measured by connecting the tube for measuring blood pressure to a pressure transducer (TP-400T; manufactured by Nihon Kohden) and recorded on a polygraph.

Results

The successive decrease in blood pressure was observed on the oral administration of 0.25 and 0.5 mg/kg of 5-amino-N-cyano-N'-[2-(2-chlorophenyl)ethyl]- 3-pyridinecarboximidamide according to the present invention (see Table 3). Table 3: Effect of 5-amino-N-cyano-N'-[2-(2chlorophenyl)ethyl]- 3-pyridinecarboximidamide (N-cyano-N'-[2-(2-chlorophenyl)ethyl]-5-( 3-aminopyridine)carboximidamide) on the blood pressure of renal hypertensive beagles

| Time after administration (hour) | Average blood pressure (mmHg) Dose (mg/kg, p.o.) | |
|---|---|---|
| | 0.25 | 0.50 |
| 0 | 122.4 ± 4.4 | 126.6 ± 0.5 |
| 1 | 100.9 ± 7.4 | 68.1 ± 7.4 |
| 2 | 85.7 ± 0.3 | 84.8 ± 6.1 |
| 4 | 102.8 ± 3.9 | 99.7 ± 12.3 |
| 6 | 110.1 ± 2.6 | 106.2 ± 9.5 |
| 8 | 112.6 ± 3.4 | 114.4 ± 7.3 |
| 24 | 118.8 ± 4.8 | 111.8 ± 3.9 |

Pharmacological Test 4: Time Course of antihypertensive activity in SHR

Time course of antihypertensive activity of 5-amino-N-cyano-N'-(2-phenethyl)pyridinecarboximidamide (Compound No. 16) was examined.

(1) Test Method

Antihypertensive activity of the compound was observed in conscious male spontaneously hypertensive rats (SHR). Systolic blood pressure (SBP) was measured with the tail cuff method.

The compound No. 16 was dissolved in an equivalent mixture of polyethylene glycol 200 and physiological saline, and administered orally with the aid of an oral probe. SBP was measured before administration and 1, 2, 4, 6, 8, 12 and 24 hours after administration of the compound. The results were expressed as the percentage change in SBP obtained before administration.

(2) Results

The decrease in blood pressure was observed after the administration of 3.0 mg/kg of the compound (16) and the antihypertensive effect lasted for 12 hours or more (see Table 4). Table 4: Antihypertensive activity of 5-amino-N-cyano-N'-( 2-phenethyl)pyridinecarboximidamide (Compound No. 16) in SHR (Data are expressed as the percentage change in SBP obtained before administration)

| Compound No. | Time after administration (hour) | | | | | | |
|---|---|---|---|---|---|---|---|
| | 1 | 2 | 4 | 6 | 8 | 12 | 24 |
| 16 | −45.3 | −23.9 | −42.3 | −27.9 | −22.8 | −15.1 | −8.2 |

Pharmacological Test 5: Acute toxicity

Acute toxicity of 5-amino-N-cyano-N'-[2-( 2-chlorophenyl)ethyl]-3-pyridinecarboximidamide (Compound No. 6) of the present invention on oral administration was examined with male SD rats (5 weeks old). As a result, no rats died at the dose of 50 mg/kg. $LD_{50}$ was in the range over 50 mg/kg.

Example 1

Preparation of 3-cyano-5-methylpyridine

3-Cyano-5-methylpyridine is a well-known compound, which may be prepared, for example, by the methods described in Published European Patent No. 253360/1988; European Journal of Biochemistry, 118, 3, 479-486 (1981); or Chemical and Pharmaceutical Bulletin, 22, 10, Synthesis of N-cyano-N'-[2-(2-chlorophenyl)ethyl]- 5-methyl-3-pyridinecarboximidamide 3-Cyano-5-methylpyridine (2 g, 16.9 mmol) was dissolved in 1-propanol (100 ml). Sodium methoxide (46 mg, 0.85 mmol) was added, and the resulting mixture was stirred at 0° C. for 20 hours. After the completion of the reaction, the reaction mixture was neutralized with acetic acid (56 mg, 0.93 mmol), and the resulting mixture was concentrated under reduced pressure. After concentration, ethyl ether (50 ml) was added to the residue, and insoluble sodium acetate was removed by filtration. The filtrate was concentrated under reduced pressure to give a crude product of propyl 5-methyl- 3-pyridinecarboximidate.

To propyl 5-methyl-3-pyridinecarboximidate was then added an aqueous solution (100 ml) of cyanamide (1.42 g, 33.8 mmol), $Na_2HPO_4$ (2.40 g, 16.9 mmol) and $NaH_2PO_4 \cdot 2H_2O$ (10.56 g, 67.7 mmol). The mixture was stirred at room temperature for 5 hours and extracted with chloroform (100 ml×3). The chloroform layer was dried over anhydrous sodium sulfate and concentrated under reduced pressure to give a crude product of propyl N-cyano-5-methyl-3-pyridinecarboximidate (2.54 g). IR (neat) $cm^{-1}$: 2200, 1610, 1320, 730.

Propyl N-cyano-5-methyl-3-pyridinecarboximidate (0.77 g, 3.8 mmol) thus obtained was next dissolved in methanol (5 ml), and 2-(2-chlorophenyl) ethylamine (0.59 g, 3.8 mmol) was added to the mixture. The resulting mixture was stirred at room temperature for 30 minutes. After the reaction mixture was concentrated under reduced pressure, it was subjected to silica gel column chromatography (Wako Gel C-200, 30 g; eluted with chloroform:methanol=100:1) and crystallized from methanol/diethyl ether to give the title compound (0.62 g, 2.1 mmol) as colorless crystals (yield, 55%). IR (KBr) $cm^{-1}$:2160, 1580, 1540, 1440, 1210, 740, 720. $^1$H-NMR (100 MHz, $CDCl_3$): δ (ppm)

8.98(1H, d, J=2.7Hz, H-6), 8.67(1H, d, J=1.8Hz, H-2), 8.27(1H, m, H-4), 7.4-7.2(4H, $C_6H_4Cl$), 3.82(2H, dd, J=6.7, 12.8Hz, $NHCH_2CH_2C_6H_4Cl$), 3.12(2H, t, J=6.7Hz, $NHCH_2CH_2C_6H_4Cl$), 2.47(3H, s, Pyridine-$CH_3$).

Example 2

Preparation of 3-cyano-5-ethylpyridine

5-Bromo-3-cyanopyridine (6.5 g) was dissolved in triethylamine (15 ml), and bis(triphenylphosphine)-palladium chloride [$(Ph_3P)_2PdCl_2$] (600 mg), cuprous iodide (CuI) (350 mg) and trimethylsilylacetylene (TMSCCH) (7.5 ml) were added. The mixture was stirred in a tight sealed reactor at 100° C. for 60 minutes. After cooling, water (50 ml) was added to the mixture and extracted with diethyl ether (50 ml×3). The diethyl ether layer was dried over anhydrous sodium sulfate and concentrated under reduced pressure to give a residue (6.87 g). The residue (4 g) was next dissolved in tetrahydrofuran (30 ml), and a iN tetrahydrofuran solution (20 ml) of tetrabutylammonium fluoride ($Bu_4NF$) was added to the solution at 5° C. The mixture was stirred for 10 minutes while allowed to raise the temperature up to room temperature. An aqueous solution of 1N sodium hydroxide (50 ml) was added to the reaction mixture and extracted with diethyl ether (50 ml×3). The diethyl ether layer was dried over anhydrous sodium sulfate, concentrated at reduced pressure and subjected to silica gel column chromatography (Wako Gel C-200, 40 g; eluted with diethyl ether:hexane= 1:1) to give 3-cyano-5-ethynylpyridine (1.84 g) as pale yellow solids (yield, 70%).

3-Cyano-5-ethynylpyridine (1 g) was dissolved in tetrahydrofuran (30 ml) and subjected to catalytic hydrogenation under hydrogen stream in the presence of 10% palladium-carbon (100 mg) as a catalyst. After the catalyst was removed by filtration, the filtrate was concentrated under reduced pressure to give 0.87 g of 3-cyano-5-ethylpyridine (yield, 84%). $^1$H-NMR (90 MHz, $CDCl_3$): δ (ppm) 8.58(1H, H-2), 8.39(1H, H-6), 7.77(1H, H-4), 2.72(2H, q, J=7.5Hz, Pyridine-$CH_2CH_3$), 1.26(3H, t, J=7.5Hz, Pyridine-$CH_2CH_3$).

Synthesis of N-cyano-N'-[2-(2-chlorophenyl)ethyl-5-ethyl-3-pyridinecarboximidamide After 3-cyano-5-ethylpyridine (2.07 g, 15.7 mmol) was dissolved in 1-propanol (80 ml) and hydrogen chloride gas was passed into the solution for 30 minutes, the reactor was tight sealed and the mixture was stirred at room temperature for 30 hours. After the completion of the reaction, the reaction mixture was concentrated under reduced pressure, and the residue was neutralized with a saturated aqueous sodium carbonate solution and extracted with chloroform (100 ml×3). The chloroform layer was washed with saturated brine, dried over anhydrous sodium sulfate and concentrated under reduced pressure to give a crude product of propyl 5-ethyl-3-pyridinecarboximidate (2.94 g).

The propyl 5-ethyl-3-pyridinecarboximidate were then dissolved in acetonitrile (5 ml), and an aqueous solution (30 ml) of cyanamide (1.13 g, 26.9 mmol), $Na_2HPO_4$ (1.29 g, 9.1 mmol) and $NaH_2PO_4 \cdot 2H_2O$ (8.45 g, 54.2 mmol) was added to the solution. The mixture was stirred at room temperature for 19 hours. After reaction, the mixture was extracted with chloroform (50 ml×2). The chloroform layer was dried over anhydrous sodium sulfate, concentrated under reduced pressure and subjected to silica gel column chromatography (Wako Gel C-200, 50 g; eluted with hexane:ethyl acetate=5:1) to give 1.51 g (7.0 mmol) of propyl N-cyano-5-ethyl-3-pyridinecarboximidate (yield, 44%).

The propyl N-cyano-5-ethyl-3-pyridinecarboximidate (276 mg, 1.27 mmol) thus obtained was next dissolved in methanol (2 ml), and 2-(2-chlorophenyl)ethylamine (238 mg, 1.53 mmol) was added to the mixture. The resulting mixture was stirred at room temperature for 75 minutes. After the completion of the reaction, the mixture was concentrated under reduced pressure, and the residue obtained was crystallized from methanol/diethyl ether to give the title compound (217 mg, 0.69 mmol) as colorless crystals (yield, 55%).

Mp 118° C.

IR (KBr) $cm^{-1}$: 3230, 2290, 1580.

FD-MS m/z 312 (M, $C_{17}H_{17}N_4Cl$).

$^1$H-NMR (500 Mltz, $CDCl_3$): δ (ppm) 8.51(1H, s, H-2), 8.43(1H, s, H-6), 7.77(1H, s, H- 4), 7.4-7.2(4H, $C_6H_4Cl$), 6.56(1H, brs, NH), 3.81(2H, dd, J=6.7, 12.8Hz, NH$CH_2$$CH_2C_6H_4Cl$), 3.15(2H, t, J=6.7Hz, NH$CH_2$$CH_2$$C_6H_4Cl$), 2.70(2H, q, J=7.6Hz, Pyridine-$CH_2CH_3$), 1.26(3H, t, J=7.6Hz, Pyridine-$CH_2$$CH_3$).

Example 3

Preparation of 3-Cyano-5-Hydroxymethylpyridine

3-Cyano-B-hydroxymethylpyridine is a well-known compound and may be prepared by the method described in U.S. Pat. No. 5,002,949.

Synthesis of N-cyano-N'-[2-(2-chlorophenyl)ethyl]-5-hydroxymethyl-3-pyridinecarboximidamide After 3-cyano-5-hydroxymethylpyridine (0.79 g, 5.9 mmol) was dissolved in 1-propanol (30 ml) and hydrogen chloride gas was passed into the solution under ice-cooling for 30 minutes, the reactor was tight sealed for stirring the mixture at room temperature for 20 hours. After the completion of the reaction, the reaction mixture was concentrated under reduced pressure, and the residue was neutralized with a saturated aqueous sodium carbonate solution and extracted with chloroform (30 ml× 3). The chloroform layer was dried over anhydrous sodium sulfate and concentrated under reduced pressure. The residue was dissolved in acetonitrile (20 ml), and an aqueous solution (30 ml) of cyanamide (0.50 g, 11.9 mmol), $Na_2HPO_4$ (0.84. g, 5.9 mmol) and $NaH_2PO_4 \cdot 2H_2O$ (3.79 g, 23.7 mmol) was added to the solution. The mixture was stirred at room temperature for 10 hours. After the completion of the reaction, the mixture was extracted with chloroform (100 ml×3). The chloroform layer was dried over anhydrous sodium sulfate and concentrated under reduced pressure to give a crude product of propyl N-cyano-5-hydroxymethyl-3-pyridinecarboximidate.

The crude product was next dissolved in methanol (10 ml), and 2-(2-chlorophenyl)ethylamine (0.5 g, 3.2 mmol) was added to the mixture. The resulting mixture was stirred at room temperature for 3 hours. After the completion of the reaction, the mixture was concentrated under reduced pressure, and the residue obtained was purified by silica gel thin layer chromatography (Merck, No. 5744; developed with chloroform: methanol=10:1) and further crystallized from methanol/diethyl ether to give the title compound (0.12 g, 0.38 mmol) as colorless powder (yield starting from 3-cyano-5-hydroxymethylpyridine, 6%).

IR (KBr) $cm^{-1}$: 3350, 2200, 1580.

FD-MS m/z 314 (M, $C_{16}H_{15}N_4OCl$).

$^1$H-NMR (90 MHz, $CDCl_3$):δ (ppm) 8.72(1H, brs, H-6), 8.68(1H, brs, H-2), 7.99(1H, m, H-4), 7.4-7.2(4H, $C_6H_4Cl$), 6.82(1H, brs, NH), 4.78(2H, $CH_2OH$), 3.82(2H, m, $NHCH_2CH_2C_6H_4Cl$), 3.12(2H, t, $NHCH_2CH_2C_6H_4Cl$).

Example 4

Preparation of 5-carbomethoxy-3-cyanopyridine

3-Cyano-5-ethynylpyridine (1.28 g) (see Example 2) was dissolved in acetone (20 ml), and an aqueous solution (40 ml) of potassium permanganate (350 mg) was added dropwise. After the addition was completed, the reaction mixture was heated to 100° C. and filtered. The filtrate was concentrated under reduced pressure, and the residue was dissolved in DMF (20 ml). Potassium carbonate (1.6 g) and dimethyl sulfate (1 ml) were added to the solution, and the mixture was stirred at room temperature for 10 minutes. Water (10 ml) was added to the reaction mixture, and resulting mixture was extracted with diethyl ether (30 ml×3). The diethyl ether layer was dried over anhydrous sodium sulfate, concentrated under reduced pressure and purified by silica gel column chromatography (Wako Gel C-200, 10 g; eluted with hexane:diethyl ether= 1:1) to give 5-carbomethoxy-3-cyanopyridine (670 mg; yield, 41%) as colorless solids. IR (KBr) $cm^{-1}$: 2210, 1730.

Synthesis of 5-carboxy,N-cyano-N'-[2-(2-chlorophenyl)ethyl]-3-pyridinecarboximidamide After 3-carbomethoxy-5-cyanopyridine (1.2 g, 7.4 mmol) was dissolved in 1-propanol (40 ml) and hydrogen. chloride gas was passed into the solution under icecooling for 20 minutes, the reactor was tight sealed for stirring the mixture at 0° C. for 22 hours. After reaction, the reaction mixture was concentrated under reduced pressure, and the residue thus obtained was neutralized with a saturated aqueous sodium carbonate solution and extracted with chloroform (50 ml×3). The chloroform layer, after washing with saturated brine, was dried over anhydrous sodium sulfate and concentrated under reduced pressure. The residue was dissolved in acetonitrile (3 ml), and an aqueous solution (16.5 ml) of cyanamide (682 mg, 16.2 mmol), $Na_2HPO_4$ (1.15 g, 8.1 mmol) and $NaH_2PO_4 \cdot 2H_2O$ (5.07 g, 32.5 mmol) was added to the solution. The mixture was stirred at room temperature for 18 hours and extracted with chloroform (50 ml x 3). The chloroform layer was dried over anhydrous sodium sulfate and concentrated under reduced pressure. The residue was purified by silica gel column chromatography (Wako Gel C-200, 40 g; eluted with hexane:ethyl acetate= 3:1) to give 1.39 g (0.56 mmol) of propyl N-cyano- 5-(3-carbomethoxy-pyridine)carboximidate (yield, 76%).

IR (KBr) $cm^{-1}$:2960, 2180, 1730, 1610, 1280.

FD-MS m/z 247 (M, $C_{12}H_{13}N_3O_3$).

$^1$H-NMR (500 MHz, $CDCl_3$): δ (ppm) 9.41(1H, d, J=1.8Hz, H-6), 9.39(1H, d, J=1.8Hz, H- 2), 8.94(1H, t, J=1.8Hz, H-4), 4.48(2H, t, J=6.4Hz, $OCH_2CH_2CH_3$), 4.01(3H, s, $COOCH_3$), 1.91(2H, m, $OCH_2CH_2CH_3$), 1.08(3H, t, J=7.6Hz, $OCH2CH_2CH_3$).

To propyl N-cyano-5-(3-carbomethoxypyridine)-carboximidate (448 mg, 1.81 mmol), after dissolved in methanol (10 ml), was added 2-(2-chlorophenyl)ethylamine (340 mg, 2.19 mmoles), and the mixture was stirred at room temperature for 105 minutes. After the completion of the reaction, ether (30 ml) was added to the reaction mixture, and white precipitates were collected by filtration and dissolved in methanol (30 ml). An aqueous solution of 40% sodium hydroxide (2 ml) was added, and the mixture was stirred at room temperature for 16 hours. The reaction mixture was neutralized on an acidic ion exchange resin Dowex 50W x 8(H+). The resin was removed by filtration, and the filtrate was concentrated under reduced pressure to give the title compound (509 mg, yield 86%) as colorless powder.

IR (KBr) $cm^{-1}$:3220, 2160, 1590, 1435, 1380, 750.

$^1$H-NMR (90 MHz, DMSO): δ (ppm) 9.62(1H, m, NH), 9.16(1H, d, J=1.76Hz, H-2), 8.75(1H, d, J=2.19Hz, H-6), 7.40(1H, dd, J=1.76, 2.19Hz, H-4), 7.2-7.2(4H, $C_6H_4Cl$), 3.70(2H, m, $NHCH_2CH2C_6H_4Cl$), 3.07(2H, t, J=6.82Hz, $NHCH_2CH_2C_6H_4Cl$).

Example 5

Preparation of 6-Amino-3-Cyanopyridine

6-Amino-3-cyanopyridine is a well-known compound and may be prepared by the methods described, for example, in Heterocycles, 22, 1, 117–124 (1984); or Journal of Heterocyclic Chemistry, 11, 3, 397–399 (1974). Synthesis of 6-amino-N-cyano-N'-[2-( 2-chlorophenyl)ethyl)-3-pyridinecarboximidamide (N-cyano-N'-[2,(2-chlorophenyl)ethyl]-5-(2-aminopyridine)carboximidamide After 6-amino-3-cyanopyridine (1.0 g, 8.4 mmol) was dissolved in 1-propanol (50 ml) and hydrogen chloride gas was passed into the solution at a temperature of 0°–10° C. for 30 minutes, the reactor was tight sealed for stirring the mixture at 0° C. for 21 hours. After the completion of the reaction, the reaction mixture was concentrated under reduced pressure, and a saturated aqueous sodium hydrogen carbonate solution (50 ml) was added to the concentrated mixture to adjust the pH to alkaline. The mixture was extracted with chloroform (50 ml×3). The chloroform layer was dried over anhydrous sodium sulfate and concentrated under reduced pressure to give a crude product of propyl 6-amino-3-pyridinecarboximidate (1.56 g).

The crude product was then dissolved in a mixture of acetonitrile (6 ml) and DMF (2 ml), and an aqueous solution (20 ml) $NaH_2PO_4 \cdot 2H_2O$ (5.24 g, 33.6 mmol), mmol) was added to the solution. The mixture was stirred at room temperature for 18 hours. After the completion of the reaction, colorless powder deposited was collected by filtration and washed with water to give propyl N-cyano-6-amino-3-pyridinecarboximidate (1.45 g, yield 85%).

Mp 150° C.

IR (KBr) cm$^{-1}$:3380, 2180, 1650, 1580, 1295.

$^1$H-NMR (500 MHz, DMSO): δ (ppm). 8.74(1H, d, J=2.4Hz, H-6), 8.04(1H, dd, J=2.4, 9.2Hz, H-4), 7.20(1H, brs, NH$_2$), 6.53(1H, d, J=9.2Hz, H-3), 4.27 (2H, t, J=6.7Hz, OCH$_2$CH$_2$CH$_3$), 1.75 (2H, m, OCH$_2$CH$_2$CH$_3$), 0.97 (3H, t, J=7.3Hz, OCH$_2$CH$_2$CH$_3$). Propyl N-cyano-6-amino-3-pyridinecarboximidate (200 mg, 0.98 mmol) and 2-(2-chlorophenyl)ethylamine (170 mg, 1.09 mmol) were dissolved in a mixture of methanol (10 ml) and DMF (1.5 ml), and the mixture was stirred at room temperature for 2.5 hours. The reaction mixture was concentrated under reduced pressure and subjected to silica gel column chromatography (Wako Gel C-200, 25 g), and elution was conducted with chloroform:methanol (30:1) to give the title compound (250 mg, yield 85%) as colorless powder.

Mp 222° C.

IR (KBr) cm$^{-1}$:3220, 2160, 1570, 740.

$^1$H-NMR (90 MHz, DMSO): δ (ppm) 8.91(1Hr brs, NH), 8.13(1H, d, J=2.5Hz, H-6), 7.60(1H, dd, J=2.5, 8.6Hz, H-4), 7.45-7.2(4H, C$_6$H$_4$Cl), 6.60(2H, brs, NH2), 6.48(1H, d, J=8.6Hz, H-3), 3.56(2H, m, NHCH$_2$CH$_2$C$_6$H$_4$Cl), 3.02(2H, t, J=7.0Hz, NHCH$_2$CH$_2$C$_6$H$_4$Cl).

Example 6

Preparation of 5-amino-3-cyanopyridine

5-Amino-3-cyanopyridine is a well-known compound and may be prepared by the methods described, for example, in Journal of Medicinal Chemistry, 10, 2, 149–154 (1967). Synthesis of 5-amino-N-cyano-N'-[2-(2-chlorophenyl)ethyl)-3-pyridinecarboximidamide (N-cyano-N'-[2-(2-chlorophenyl)ethyl]-5-(3-aminopyridine)carboximidamide After 5-amino-3-cyanopyridine (380 mg, 3.19 mmol) was dissolved in 1-propanol (15 ml) and hydrogen chloride gas was passed into the solution at a temperature of 0°–5° C. for 15 minutes, the reactor was tight sealed for stirring the mixture at room temperature for 22 hours. After the completion of the reaction, the solvent was evaporated under reduced pressure, and a saturated aqueous sodium hydrogen carbonate solution (50 ml) was added to the concentrated mixture to adjust the pH to alkaline. The mixture was extracted with chloroform (50 ml×3). The chloroform layer was dried over anhydrous sodium sulfate, concentrated under reduced pressure and subjected to silica gel column chromatography (Wako Gel C-200, 25 g), and elution was conducted with chloroform: methanol (8:1) to give propyl 5-amino- 3-pyridinecarboximidate (526 mg, yield 92%) as a colorless oil.

IR (neat) cm$^{-1}$:3330, 3200, 1630, 1590, 1080.

$^1$H-NMR (90 MHz, CDCl$_3$): δ (ppm) 8.37(1H, brs, H-2), 8.14(1H, d, J=2.6Hz, H-6), 7.31(1H, m, H-4), 4.18(2H, t, J=6.6Hz, OCH$_2$CH$_2$CH$_3$), 1.77(2H, m, OCH$_2$CH$_2$CH$_3$), 1.03(3H, t, J=7.0Hz, OCH$_2$CH$_2$CH$_3$).

The propyl 5-amino-3-pyridinecarboximidate (110 mg, 0.6 mmol) was then dissolved in acetonitrile (1 ml), and an aqueous solution (2 ml) of $NaH_2PO_4 \cdot 2H_2O$(375 mg, 2.4 mmol), $Na_2HPO_4$ (85 mg, 0.6 mmol) and $NH_2CN$ (50 mg, 1.2 mmol) was added to the solution. The mixture was stirred at room temperature for 19 hours. After the completion of the reaction, the reaction mixture was extracted with chloroform (20 ml×3), and the chloroform layer was dried over anhydrous sodium sulfate and concentrated under reduced pressure to give a crude oil of propyl 5-amino-N-cyano-3-pyridinecarboximidate (100 mg, yield 82%).

IR (neat) cm$^{-1}$:3350, 2200, 1610, 1320, 760.

$^1$H-NMR (90 MHz, CDCl$_3$): δ (ppm) 8.51(1H, d, J=2.0Hz, H-2), 8.27(1H, d, J=2.6Hz, H-6), 7.72(1H, dd, J=2.0, 2.6Hz, H-4), 4.39(2H, t, J=6.6Hz, OCH$_2$CH$_2$CH$_3$), 4.12(2H, brs, NH$_2$), 1.83(2H, m, OCH$_2$CH$_2$CH$_3$), 1.05 (3H, t, J=7.7Hz, OCH$_2$CH$_2$CH$_3$).

To a solution of propyl 5-amino-N-cyano-3-pyridinecarboximidate (100 mg, 0.49 mmol) in methanol (1 ml), 2-(2-chlorophenyl)ethylamine(155 mg, 1.0 mmol) was added, and the mixture was stirred at room temperature for 20 hours. After the completion of the reaction, the reaction mixture was concentrated under reduced pressure, and the residue was crystallized from diethyl ether/ethyl acetate to give the title compound (100 mg, 0.33 mmol, yield 68%) as colorless crystals.

Mp 184° C.

IR (neat) cm$^{-1}$:3200, 2170, 1570.

FD-MS m/z 299 (M, C$_{15}$H$_{14}$N$_5$Cl).

$^1$H-NMR (90 MHz, CD$_3$OD): δ (ppm) 8.08(1H, d, J=2.6Hz, H-6), 7.83(1H, brs, H-2), 7.5-7.2(5H, H-4, C$_6$H$_4$Cl), 3.73(2H, t, J=7.3Hz, NHCH$_2$CH$_2$C$_6$H$_4$Cl), 3.13(2H, t, J=7.3Hz, NHCH$_2$CH$_2$C$_6$H$_4$Cl).

Example 7

Synthesis of 5-acetamide-N-cyano-N'-[2-(2chlorophenyl)ethy]-3-3-pyridinecarboximidamide (N-cyano-N'-[2-(2-chlorophenyl)ethyl]-5-[3-(N-acetylamino)pyridine]carboximidamide To a solution of 5-amino-N-cyano-N'-[2-(2chlorophenyl)ethyl]- 3-pyridinecarboximidamide (100 mg, 0.33 mmol) in pyridine (1 ml) was added acetic anhydride (20 mg, 0.34 mmol), and the mixture was stirred at room temperature for 5.5 hours. After the reaction was completed, the reaction mixture was poured into ice-water, and precipitates produced was collected by filtration, washed with cold water and crystallized from methanol/diethyl ether to give the title compound (86 mg, yield 75%) as colorless powder.

Mp 230° C.

IR (KBr) cm$^{-1}$:3230, 2160, 1700, 1580, 720.

FD-MS m/z 341 (M, C$_{17}$H$_{16}$N$_5$OCl).

$^1$H-NMR (90 MHz, DMSO): δ (ppm) 10.43(1H, brs, NHCOCH3), 9.41(1H, brs, NH), 8.87(1H, d, J=2.4Hz, H-6), 8.33-1H, d, J=2.0Hz, H-2), 8.24(1H, dd, J=2.0, 2.4Hz, H-4), 7.5-7.3(4H, C$_6$H$_4$Cl), 3.63 (2H, m, NHCH$_2$CH$_2$C$_6$H$_4$Cl), 3.08 (2H, t, J=3.2Hz, NHCH$_2$CH$_2$C$_6$H$_4$Cl), 2.12(3H, s, NHCOCH$_3$).

Example 8

5-Benzamido-N-cyano-N'-[2-(2-chlorophenyl)ethyl]-3-pyridinecarboximidamide

To a solution of 5-amino-N-cyano-N'-[2-(2-chlorophenyl)ethyl]- 3-pyridinecarboximidamide (100 mg, 0.33 mmol) in DMF (3 ml) were added triethylamine (101 mg, 1 mmol) and benzoyl chloride (94 mg, 0.67 mmol), and the mixture was stirred at room temperature for 3 hours. After the reaction was completed, the reaction mixture was neutralized by adding ice and a saturated aqueous sodium carbonate solution and extracted with ethyl acetate. The ethyl acetate layer was washed with saturated brine, dried over anhydrous sodium sulfate and concentrated under reduced pressure. The residue thus obtained was purified by silica gel column chromatography (Wako Gel C-200, 30 g; eluted with chloroform:methanol= 200:1) to give the title compound (38 mg, 0.09 mmol, yield 29%).

Mp 220° C.

IR (KBr) cm$^{-1}$:3260, 2160, 1655, 1555, 1430.

FD-MS m/z 404 (M, C$_{22}$H$_{18}$N$_5$OCl).

$^1$H-NMR (90 MHz, DMSO): δ (ppm) 10.71(1H, brs, NHCOPh) , 9.46(1H, brs, NHCH$_2$CH$_2$C$_6$H$_4$Cl), 9.11(1H, d, J=2.2Hz, H-6), 8.5-8.3(2H, H-2, H-4), 8.1-7.3(9H, Ph, C$_6$H$_4$Cl) 3.63(2H, m, NHCH$_2$CH$_2$C$_6$H$_4$Cl) , 3.08(2H, t, J=7.2Hz, NHCH$_2$CH$_2$C$_6$H$_4$Cl).

Example 9

Preparation of 3-cyano-5-dimethylaminopyridine

To a solution of 5-amino-3-cyanopyridine (0.50 g, 4.20 mmol) in DMF (5 ml) was added NaH (60% in oil) (0.37 g, 9.26 mmol) under ice-cooling, and the mixture was stirred for 20 minutes. Methyl iodide (0.58 ml, 9.31 mmol) in DMF (2 ml) was added dropwise under ice-cooling. The mixture was stirred for 2 hours while the temperature was raised up to room temperature. Ice was added to the reaction mixture, and the mixture was extracted with diethyl ether (30 ml×3). The diethyl ether layer was washed with saturated brine, dried over anhydrous sodium sulfate and concentrated under reduced pressure. The residue thus obtained was purified by silica gel column chromatography (Wako Gel C-200, 20 g; eluted with chloroform:methanol=200:1) to give 3-cyano-5-dimethylaminopyridine (145 mg, yield 23%).

Mp 104° C.

IR (KBr) cm$^{-1}$:2230, 1595, 1450, 1375, 1235, 695.

$^1$H-NMR (90 MHz, CDCl$_3$): δ (ppm) 8.28(1H, d, J=3.1Hz, H-6), 8.18(1H, d, J=1.5Hz, H-2), 7.09(1H, dd, J=1.5, 3.1Hz, H-4), 3.03(6H, s, N(CH$_3$)$_2$).

Synthesis of N-cyano-N'-[2-(2-chlorophenyl)ethyl]-5-dimethylamino-3-pyridinecarboximidamide Into a solution of 3-cyano-5-dimethylaminopyridine (140 mg, 0.95 mmol) in 1-propanol (15 ml) was passed hydrogen chloride gas under ice-cooling for 30 minutes. The reactor was tight sealed, and the mixture was stirred at room temperature for 20 hours. After the reaction was completed, the reaction mixture was concentrated under reduced pressure, and the residue was neutralized with sodium carbonate and extracted with chloroform (50 ml× 3). The chloroform layer was dried over anhydrous sodium sulfate and concentrated under reduced pressure. The residue was dissolved in acetonitrile (5 ml) and an aqueous solution (10 ml) of cyanamide (80 mg, 1.9 mmol), Na$_2$HPO$_4$ (135 mg, 0.95 mmol) and NaH$_2$PO$_4$·2H$_2$O (593 mg, 3.80 mmol) was added to the solution. The mixture was stirred at room temperature for 10 hours. After the reaction was completed, the reaction mixture was extracted with chloroform (30 ml), and the chloroform layer was dried over anhydrous sodium sulfate and concentrated under reduced pressure to give a pale yellow syrup.

To a solution of this syrup dissolved in methanol (10 ml) was added 2-(2-chlorophenyl)ethylamine (170 mg, 1.09 mmol), and the mixture was stirred at room temperature for 4 hours. After the reaction was completed, the reaction mixture was concentrated under reduced pressure, and the residue was purified by silica gel column chromatography (Wako Gel C-200, 20 g; eluted with chloroform:methanol= 100:1) and further crystallized from methanol/diethyl ether to give the title compound (219 mg, 0.67 mmol) in the yield of 70%.

Mp 158° C.

IR (KBr) cm$^{-1}$:3400, 2160, 1575, 1430.

FD-MS m/z 327 (M, C$_{17}$H$_{18}$N$_5$Cl).

$^1$H-NMR (90 MHz, DMSO): δ (ppm) 9.25(1H, brs, NHCH$_2$CH$_2$C$_6$H$_4$Cl), 8.26(1H, d, J=2.9Hz, H-6), 7.95(1H, d, J=1.8Hz, H-2), 7.5-7.2(4H, C$_6$H$_4$Cl), 7.11(1H, dd, J=1.8, 2.9Hz, H-4), 3.63(2H, m, NHCH$_2$CH$_2$C$_6$H$_4$Cl), 3.05( 2H, m, NHCH$_2$CH$_2$C$_6$H$_4$Cl), 2.98(6H, s, N(CH$_3$)$_2$).

Example 10

Preparation of 3-Cyano-5-Ethylaminopyridine

To a solution of 5-amino-3-cyanopyridine (300 mg, 2.52 mmol) in methanol (10 ml) was added acetaldehyde (1.42 ml, 25.1 mmol), and the mixture was stirred at room temperature for 10 minutes. Next, sodium cyanoborohydride (950 mg, 15.1 mmol) was added, and acetic acid was further added to adjust the pH of thereaction mixture to about 6. The mixture was stirred for 5 hours. After the reaction was completed, the reaction mixture was neutralized with an aqueous sodium carbonate solution and extracted with diethyl ether (30 ml×3). The diethyl ether layer was dried over anhydrous sodium sulfate and concentrated under reduced pressure. The residue thus obtained was purified by silica gel column chromatography (Wako Gel C-200, 20 g; eluted with chloroform:methanol=200:1) to give 3-cyano-5-ethylaminopyridine (200 mg, 1.36 mmol, yield 54%).

Mp 110° C.

IR (neat) cm$^{-1}$:2210, 1585, 1450, 1180, 690.

$^1$H-NMR (90 MHz, CDCl$_3$): δ (ppm) 8.2-8.1(2H, H-2, H-6), 6.99(1H, dd, J=1.8, 2.9Hz, H- 4), 4.08(1H, brs, NH), 3.61(2H, m, NHCH$_2$CH$_3$), 1.25(3H, d, J=6.4Hz, NHCH$_2$CH$_3$).

Synthesis of N-cyano-N'-[2-(2-chlorophenyl)ethyl]-5-ethylamino-3-pyridinecarboximidamide Into a solution of 3-cyano-5-ethylaminopyridine (380 mg, 2.59 mmol) in 1-propanol (40 ml) was passed hydrogen chloride gas under ice-cooling for 30 minutes. The reactor was tight sealed, and the mixture was stirred at room temperature for 20 hours and concentrated under reduced pressure. After the residue was neutralized with a saturated aqueous sodium carbonate solution and extracted with chloroform (50 ml×3). The chloroform layer was dried over anhydrous sodium sulfate and concentrated under reduced pressure to give a crude product of propyl 5-ethylamino-3-pyridinecarboximidate. The crude product was then dissolved in acetonitrile (5 ml) and an aqueous solution (18 ml) of cyanamide (210 mg, 5.0 mmol), $Na_2HPO_4$ (355 mg, 2.5 mmol) and $NaH_2PO_4 \cdot 2H_2O$ (1.56 g, 10 mmol) was added to the solution, and the mixture was stirred at room temperature over night. After the reaction was completed, the reaction mixture was extracted with chloroform (30 ml×3), and the chloroform layer was dried over anhydrous sodium sulfate and concentrated under reduced pressure. The residue obtained was purified by silica gel column chromatography (Wako Gel C-200, 30 g; eluted with hexane/ethyl acetate) to give propyl N-cyano-5-ethylamino-3-pyridinecarboximidate (322 mg, 1.38 mmol) as a colorless oil (Yield 54%).

IR (KBr) $cm^{-1}$:2960, 2200, 1600, 1460, 1330.

$^1$H-NMR (90 MHz, $CDCl_3$): δ (ppm) 8.41(1H, d, J=2.0Hz, H-6), 8.18(1H, d, J=2.9Hz, H- 2), 7.61(1H, dd, J=2.0, 2.9Hz, H-4), 4.39(2H, t, J=6.5Hz, O C$\underline{H}_2$CH$_2$CH$_3$), 3.95(1H, brs, NH), 3.22(2H, m, NH C$\underline{H}_2$CH$_3$), 1.82(2H, m, OCH$_2$C$\underline{H}_2$CH$_3$), 1.31(3H, t, J=7.2Hz, NHCH$_2$C$\underline{H}_3$), 1.06(3H, t, J=6.8Hz, OCH$_2$CH$_2$C$\underline{H}_3$).

To a solution of propyl N-cyano-5-ethylamino-3-pyridinecarboximidate (98 mg, 0.42 mmol) in methanol (3 ml) was added 2-(2-chlorophenyl)ethylamine(79 mg, 0.51 mmol), and the mixture was stirred for 105 minutes. The residue obtained by concentration under reduced pressure was purified by silica gel column chromatography (Wako Gel C-200, 30 g; eluted with chloroform:methanol= 100:1) and further crystallized from diethyl ether to give the title compound (110 mg, 0.34 mmol) as colorless crystals in the yield of 80%.

Mp 168° C.

IR (KBr) $cm^{-1}$:3230, 2170, 1560, 1445, 750.

FD-MS m/z 327 (M, $C_{17}H_{18}N_5Cl$).

$^1$H-NMR (90 MHz, $CDCl_3$): δ (ppm) 7.95(1H, d, J=2.6Hz, H-6), 7.79(1H, d, J=1.8Hz, H- 2), 7.4-7.0(5H, H-4, $C_6H_4Cl$), 4.35(1H, brs, N$\underline{H}$CH$_2$C$_6$H$_4$Cl), 3.76(2H, m, NHC$\underline{H}_2$CH$_2$C$_6$H$_4$Cl), 3.3-2.9(4H, NHCH$_2$ C$\underline{H}_2$C$_6$H$_4$Cl, NHC$\underline{H}_2$), 2.88(1H, brs, N$\underline{H}$CH$_2$CH$_3$), 1.26(3H, t, J=7.1Hz, NHCH$_2$C$\underline{H}_3$).

Example 11

Preparation of 3-Cyano-5Isopropylaminopyridine

In the similar manner as in the preparation of 3-cyano-5-ethylaminopyridine, 3-cyano-5-isopropylaminopyridine was obtained.

Mp 82° C.

IR (neat) $cm^{-1}$:2210, 1585, 1450, 1180, 690.

$^1$H-NMR (90 MHz, $CDCl_3$): δ (ppm) 8.2-8.1(2H, H-2, H-6), 6.99(1H, dd, J=1.8, 2.9Hz, H- 4), 4.08(1H, brs, NH), 3.61(1H, m, NHC$\underline{H}$(CH$_3$)$_2$), 1.25(6H, d, J=6.4Hz, NHCH(C$\underline{H}_3$)$_2$).

N-cyano-N'-[2-(2-chlorophenyl)ethyl]-5-isopropylamino- 3-pyridinecarboximidamide Into a solution of 3-cyano-5-isopropylaminopyridine (118 mg, 0.73 mmol) in 1-propanol (20 ml) was passed hydrogen chloride gas under ice-cooling for 30 minutes. The reactor was tight sealed, and the mixture was stirred at room temperature for 17 hours. After the reaction was completed, the reaction mixture was concentrated under reduced pressure, and the residue was neutralized with a saturated sodium carbonate solution and extracted with chloroform (50 ml×3). The chloroform layer was dried over anhydrous sodium sulfate and concentrated under reduced pressure to give a yellow syrup. To the syrup was then added an aqueous solution (6 ml) of cyanamide (61 mg, 1.45 mmol), $Na_2HPO_4$ (104 mg, 0.73 mmol) and $NaH_2PO_4 \cdot 2H_2O$ (456 mg, 2.92 mmol), and the mixture was stirred at room temperature for 22 hours. After the reaction was completed, the reaction mixture was extracted with chloroform (30 ml×3), and the chloroform layer was dried over anhydrous sodium sulfate and concentrated under reduced pressure to give propyl N-cyano- 5-isopropylamino-3-pyridinecarboximidate (80 mg, 0.33 mmol) as a yellow syrup (Yield 44%).

IR (neat) $cm^{-1}$:2950, 2180, 1580, 1445, 1310.

$^1$H-NMR (500 MHz, $CDCl_3$): δ (ppm) 8.38(1H, d, J=1.8Hz, H-6), 8.16(1H, d, J=3.1Hz, H-2), 7.58(1H, dd, J=1.8, 3.1Hz, H-4), 4.38(2H, t, J=6.4Hz, O C$\underline{H}_2$CH$_2$CH$_3$), 4.09(1H, brs, NH), 3.66(1H, m, NH C$\underline{H}$(CH$_3$)$_2$), 1.86 (2H, m, OCH$_2$C$\underline{H}_2$CH$_3$), 1.26 (6H, d, J=6.1Hz, NCH(C$\underline{H}_3$)$_2$), 1.05(3H, t, J=7.3Hz , OCH$_2$CH$_2$C$\underline{H}_3$).

To a solution of propyl N-cyano-5-isopropylamino-3-pyridinecarboximidate (98 mg, 0.42 mmol) in methanol (3 ml) was added 2-(2-chlorophenyl)ethylamine (79 mg, 0.51 mmol), and the mixture was stirred for 105 minutes. After the reaction was completed, the reaction mixture was concentrated under reduced pressure and the residue obtained was purified by silica gel column chromatography (Wako Gel C-200, 30 g; eluted with chloroform:methanol= 100:1) and further crystallized from diethyl ether to give the title compound (110 mg, 0.34 mmol) as colorless crystals in the yield of 80%.

IR (KBr) $cm^{-1}$:2960, 2160, 1555, 1440.

$^1$H-NMR (90 MHz, $CDCl_3$): δ (ppm) 7.98(1H, d, J=2.6Hz, H-6), 7.78(1H, d, J=1.8Hz, H-2), 7.5-7.2(4H, $C_6H_4Cl$), 7.12(1H, dd, J=1.8, 2.6Hz, H-4), 6.62(1H, brt, N$\underline{H}$CH$_2$CH$_2$C$_6$H$_4$Cl), 4.11(1H, N$\underline{H}$CH(CH$_3$)$_2$), 3.76(2H, m, NHC$\underline{H}_2$CH$_2$C$_6$H$_4$Cl), 3.46( 1H, m, NH C$\underline{H}$(CH$_3$)$_2$), 3.14( 2H, t, J=6.6Hz, NHCH$_2$ C$\underline{H}_2$C$_6$H$_4$Cl), 1.24(6H, d, J=6.4Hz, NHCH(C$\underline{H}_3$)$_2$).

Example 12

Preparation of 5-N-Butylamino-3-Cyanopyridine

In the similar manner as in the preparation of 3-cyano-5-ethylaminopyridine , 5-n-butylamino-3-cyanopyridine was obtained.

Mp 73° C.

IR (KBr) $cm^{-1}$:3270, 2240, 1590, 1440, 690.

$^1$H-NMR (90MHz, $CDCl_3$): δ (ppm) 8.2-8.1(2H, H-2, H-6), 6.99(1H, dd, J=2.0, 2.6Hz, H-4), 3.96(1H, brs, NH), 3.13(2H, m, NHC$\underline{H}_2$CH$_2$CH$_2$CH$_3$), 1.6-1.3( 4H, NHCH$_2$C$\underline{H}_2$C$\underline{H}_2$CH$_3$), 0.98(3H, t, J=6.4Hz, NHCH$_2$CH$_2$CH$_2$C$\underline{H}_3$).

Synthesis of 5-n-butylamino-N-cyano-N'-[2-(2-chlorophenyl)ethyl]-3-pyridinecarboximidamide Into a solution of 5-n-butylamino-3-cyanopyridine (255 mg, 1.46 mmol) in 1-propanol (30 ml) was passed hydrogen chloride gas under ice-cooling for 30 minutes. The reactor was tight sealed, and the mixture was stirred at-room temperature for 16 hours. After the reaction was completed, the reaction mixture was concentrated under reduced pressure, and the residue was neutralized with a saturated aqueous sodium carbonate solution and extracted with chloroform (50 m×3). The chloroform layer was dried over anhydrous sodium sulfate and concentrated under reduced pressure to give a syrup.

To a solution of the syrup in acetonitrile (3 ml) was then added an aqueous solution (20 ml) of cyanamide (123 mg, 2.93 mmol), $Na_2HPO_4$ (207 mg, 1.46 mmol) and $NaH_2PO_4 \cdot 2H_2O$ (911 mg, 5.84 mmol), and the mixture was stirred at room temperature for 22 hours. The reaction mixture was extracted with chloroform (30 ml×3), and the chloroform layer was dried over anhydrous sodium sulfate and concentrated under reduced pressure. The residue was purified by silica gel column chromatography (Wako Gel C-200, 30 g; eluted with hexane:ethyl acetate= 4:1) to give propyl 5-n-butylamino-N-cyano-3-pyridinecarboximidate (252 mg, 0.97 mmol) as a yellow syrup.

IR (neat) $cm^{-1}$:2950, 2170, 1590, 1460, 1320.

$^1$H-NMR (90 MHz, $CDCl_3$): δ (ppm) 8.40(1H, d, J=2.0Hz, H-6), 8.19(1H, d, J=2.9Hz, H-2), 7.57(1H, dd, J=2.0, 2.9Hz, H-4), 4.39(2H, t, J=6.6Hz, O$\underline{CH_2}$CH$_2$CH$_3$), 3.16( 2H, m, NH$\underline{CH_2}$CH$_2$CH$_2$CH$_3$), 2.0-1.2 (6H, 3×CH$_2$), 1.1-0.8(6H, 2×CH$_3$).

To a solution of propyl 5-n-butylamino-N-cyano-3-pyridinecarboximidate (99 mg, 0.38 mmol) in methanol (2 ml) was added 2-(2-chlorophenyl)ethylamine (71 mg, 0.46 mmol), and the mixture was stirred for 2 hours. After the reaction was completed, the reaction mixture was concentrated under reduced pressure and the residue obtained was purified by silica gel column chromatography (Wako Gel C-200, 30 g; eluted with chloroform:methanol= 200:1) and further crystallized from diethyl ether to give the title compound (90 mg, 0.25 mmol) as colorless crystals in the yield of 67%.

Mp 122° C.

IR (KBr) $cm^{-1}$:2950, 2160, 1560, 1460, 750.

FD-MS m/z 355 (M, $C_{19}H_{22}N_5Cl$).

$^1$H-NMR (90 MHz, $CDCl_3$): δ (ppm) 7.92(1H, d, J=2.6Hz, H-6), 7.77(1H, d, J=1.8Hz, H-2), 7.5-7.1(4H, C6H4Cl), 7.07(1H, dd, J=1.8, 2.6Hz, H-4), 4.46(1H, brt, NH), 3.75(2H, m, NH$\underline{CH_2}$C$_6$H$_4$Cl), 3.2-2.8(4H, 2×CH$_2$), 1.7-1.2(4H, 2×CH$_2$), 0.95(3H, t, J=6.8Hz, CH$_3$).

Example 13

Preparation of 5-Benzylamino-3-Cyanopyridine

In the similar manner as in the preparation of 3-cyano-5-ethylaminopyridine, 5-benzylamino-3-cyanopyridine was obtained.

Mp 131° C.

IR (KBr) $cm^{-1}$:3220, 2220, 1610, 1580, 700.

$^1$H-NMR (90 MHz, $CD_3OD$): δ (ppm) 8.36(1H, d, J=1.5Hz, H-2), 8.23(1H, d, J=2.9Hz, H-6), 7.91(1H, dd, J=1.5, 2.9Hz, H-4), 7.5-7.2(5H, CH$_2$$\underline{Ph}$), 4.48(2H, s, $\underline{CH_2}$Ph).

Synthesis of
5-Benzylamino-N-Cyano-N'-[2-(2-chlorophenyl)ethyl]-3-pyridinecarboximidamide Into a solution of 5-benzylamino-3-cyanopyridine (250 mg, 1.19 mmol) in 1-propanol (30 ml) was passed hydrogen chloride gas under ice-cooling for 30 minutes. The reactor was tight sealed, and the mixture was stirred at room temperature for 16 hours. After the reaction was completed, the reaction mixture was concentrated under reduced pressure, and the residue was neutralized with an aqueous sodium carbonate solution and extracted with chloroform (50 ml×3). The chloroform layer was dried over anhydrous sodium sulfate and concentrated under reduced pressure.

To the solution of the residue in acetonitrile ( 2 ml) was then added an aqueous solution (20 ml) of cyanamide (100 mg, 2.38 mmol), $Na_2HPO_4$ (170 mg, 1.20 mmol) and $NaH_2PO_4 \cdot 2H_2O$ (743 mg, 4.76 mmol), and the mixture was stirred at room temperature for 24 hours. The reaction mixture was extracted with chloroform (50 ml× 3), and the chloroform layer was dried over anhydrous sodium sulfate and concentrated under reduced pressure. The residue was purified by silica gel column chromatography (Wako Gel C-200, 30 g; eluted with hexane:ethyl acetate=4:1) to give propyl 5-benzylamino-N-cyano-3-pyridinecarboximidate (206 mg, 0.7 mmol) as a syrup.

To a solution of propyl 5-benzylamino-N-cyano-3-pyridinecarboximidate (114 mg, 0.38 mmol) in methanol (2 ml) was added 2-(2-chlorophenyl)ethylamine (72 mg, 0.46 mmol), and the mixture was stirred for 105 minutes. After the reaction was completed, the reaction mixture was concentrated under reduced pressure and the residue obtained was purified by silica gel column chromatography (Wako Gel C-200, 20 g; eluted with chloroform:methanol= 200:1) and further crystallized from diethyl ether to give the title compound (126 mg, 0.32 mmol) as colorless crystals in the yield of 85%.

Mp 146° C.

IR (KBr) $cm^{-1}$:2180, 1560, 1445, 750.

FD-MS m/z 389 (M, $C_{22}H_{20}N_5Cl$).

$^1$H-NMR (90 MHz, $CDCl_3$): δ (ppm) 7.94(1H, d, J=2.6Hz, H-6), 7.82(1H, d, J=1.8Hz, H-2), 7.4-7.0(10H), 4.92(1H, brs, NH), 4.29(2H, brd, J=5.5Hz, NH$\underline{CH_2}$Ph), 3.8-3.6( 3H, NH, NH$\underline{CH_2}$CH$_2$C$_6$H$_4$Cl), 3.09(2H, t, J=6.6Hz, NHCH$_2$$\underline{CH_2}$C$_6$H$_4$Cl).

Example 14

Synthesis of N-cyano-N'-[2-(2-chlorophenyl)ethyl]-5-methanesulfonamido-3-pyridinecarboximidamide (N-cyano-N'-[ 2-(2-chlorophenyl)ethyl]-5-[ 3-(N-methanesulfonylamino)pyridine]-carboximidamide)

To a solution of 5-amino-N-cyano-N'-[2-( 2-chlorophenyl)ethyl]-3-pyridinecarboximidamide (110 mg, 0.39 mmol) in pyridine (2 ml) was added anhydrous methanesulfonic acid (65 mg, 0.37 mmol), and the mixture was stirred at room temperature for 5 hours. After the reaction was completed, ice and a saturated aqueous sodium carbonate solution (20 ml) were added to the reaction mixture, and the mixture was extracted with ethyl acetate (30 ml×3). The ethyl acetate layer was washed with saturated brine, dried over anhydrous sodium sulfate and concentrated under reduced pressure. The residue obtained was subjected to silica gel column chromatography (Wako Gel C-200, 20 g) and eluted with chloroform:methanol (50:1) to give the title compound (45 mg, yield 32%) as colorless powder.

Mp 205° C.

IR (KBr) $cm^-$:3400, 2150, 1590, 1555, 1150.

FD-MS m/z 378 (M+1, $C_{16}H_{16}N_5O_2SCl$).

$^1$H-NMR (90 MHz, DMSO): δ (ppm) 10.42(1H, brs, $\underline{NH}$SO$_2$CH$_3$), 9.46(1H, brs, NH), 8.87(1H, d, J=2.4Hz, H-6), 8.39(1H, d, J=2.0Hz, H-2), 7.76(1H, dd, J=2.0, 2.4Hz, H-4), 7.5-7.3(4H, Ph), 3.66(5H, NH C$\underline{H}_2$CH2Ph, NHSO$_2$C$\underline{H}_3$), 3.16(2H, NHCH$_2$C$\underline{H}_2$Ph).

Example 15

Synthesis of N-cyano-N'-[2-( 2-chlorophenyl)ethyl]-5-bis-(methanesulfonylamino)- 3-pyridinecarboximidamide (N-cyano-N'-[2-( 2-chlorophenyl)ethyl]-5-[ 3-(N,N-bis-methanesulfonylamino)pyridine]carboximidamide)

To a solution of 5-amino-N-cyano-N'-[2-(2chlorophenyl) ethyl]- 3-pyridinecarboximidamide (108 mg, 0.36 mmol) in a mixture of acetonitrile (1 ml) and DMF (1 ml) was added triethylamine (144 mg, 1.43 mmol) and methanesulfonyl chloride (88 mg, 0.77 mmol), and the mixture was stirred at room temperature for 2.5 hours. After the reaction was completed, the reaction mixture was poured into ice and saturated brine and extracted with ethyl acetate (30 ml×3). The ethyl acetate layer was washed with saturated brine, dried over anhydrous sodium sulfate and concentrated under reduced pressure. The residue obtained was subjected to silica gel column chromatography (Wako Gel C-200, 20 g) and eluted with chloroform:methanol (100:1) to give the title compound (89 mg, yield 54%) as colorless powder.

Mp 210° C.

IR (KBr) cm$^{-1}$:3230, 2160, 1580.

$^1$H-NMR (90 MHz, DMSO): δ (ppm) 9.60(1H, brs, NH), 8.94(1H, d, J=2.4Hz, H-6), 8.83(1H, d, J=1.8Hz, H-2), 8.23(1H, dd, J=1.8, 2.4Hz, H-4), 7.4-7.2(4H, Ph), 3.83(8H, 2×NHSO$_2$C$\underline{H}_3$ , NHC$\underline{H}_2$CH$_2$Ph), 3.08(2H, t, J=7.8Hz, NHCH$_2$C$\underline{H}_2$Ph).

Example 16

Synthesis of 5-amino-N-cyano-N'- (2-phenethyl)-3-pyridinecarboximidamide

To a solution of propyl 5-amino-N-cyano- 3-pyridinecarboximidate (310 mg, 1.51 mmol) in methanol (5 ml) was added phenethylamine (230 mg, 1.90 mmol), and the mixture was stirred at room temperature for 2 hours. After the reaction was completed, the reaction mixture was concentrated under reduced pressure and the residue was crystallized from methanol/diethyl ether to give the title compound (222 mg, 0.84 mmol) as pale yellow crystals (Yield 56%).

Mp 158° C.

IR (KBr) cm$^{-1}$:3200, 2160, 1580, 1550, 1430. $^1$H-NMR (90 MHz, DMSO): δ (ppm) 9.21(1H, brd, NH), 8.07(1H, d, J=2.6Hz, H-6), 7.76(1H, d, J=2.0Hz, H-2), 7.4-7.2(5H, Ph), 7.00(1H, dd, J=2.0, 2.6Hz, H-4), 5.70(2H, brs, NH$_2$), 3.58(2H, m, NHC$\underline{H}_2$CH$_2$Ph), 2.88(2H, t, J=6.9Hz, NHCH$_2$C$\underline{H}_2$Ph).

Example 17

Preparation of 3-Cyano-5-Hydroxypyridine

5-Hydroxynicotinamide (0.69 g, 5 mmol) prepared by the method described in International Patent Publication No. 8606628 was dissolved in pyridine (50 ml). Trifluoroacetic anhydride (2.52 g, 12 mmol) was added, and the mixture was stirred at 0° C. for 20 hours. The reaction mixture, to which water (20 ml) was added, was concentrated under reduced pressure and extracted with chloroform (50 ml×3). The chloroform layer was washed with water (50 ml), dried over anhydrous sodium sulfate and concentrated under reduced pressure to give a residue. The residue was purified by silica gel column chromatography (Wako Gel C-200, 20 g; eluted with chloroform:methanol=100:1) to give 3-cyano-5-hydroxypyridine (0.42 g, 3.5 mmol) (Yield 70%).

IR (neat) cm$^{-1}$:3250, 2920, 2180.

$^1$H-NMR (90 MHz, CDCl$_3$-CD$_3$OD): δ (ppm) 8.86(1H, d, J=1.9Hz, H-2), 8.40(1H, d, J=2.5Hz, H-6), 7.42(1H, dd, J=1.9, 2.5Hz, H-4).

Synthesis of N-cyano-N'-[2-(2-chlorophenyl)ethyl]-5-hydroxy-3-pyridinecarboximidamide Into a solution of 3-cyano-5-hydroxypyridine (0.42 g, 3.50 mmol) in 1-propanol (40 ml) was passed hydrogen chloride gas under ice-cooling for 30 minutes. The reactor was tight sealed, and the mixture was stirred at room temperature for 20 hours. After the reaction was completed, the reaction mixture was concentrated under reduced pressure. To the solution of the residue in acetonitrile (20 ml) was then added an aqueous solution (30 ml) of cyanamide (0.88 g, 20.9 mmol), Na$_2$HPO$_4$ (1.5 g, 10.6 mmol) and NaH$_2$PO$_4$·2H$_2$O (3.27 g, 21.0 mmol), and the mixture was stirred at room temperature for 6 hours. The reaction mixture was adjusted to pH 7.0 with a saturated aqueous sodium hydrogen carbonate solution and extracted with chloroform (50 ml×3). The chloroform layer was dried over anhydrous sodium sulfate and concentrated under reduced pressure to give a crude product of propyl N-cyano-5-hydroxy-3-pyridinecarboximidate (0.26 g).

To a solution of propyl N-cyano-5-hydroxy-3-pyridinecarboximidate (0.26 g) in methanol (5 ml) was added 2-(2-chlorophenyl)ethylamine (0.22 g, 1.4 mmol), and the mixture was stirred for 4 hours. After the reaction was completed, the reaction mixture was concentrated under reduced pressure and the residue obtained was extracted with chloroform (50 ml×3). The chloroform layer was washed with water (100 ml), dried over anhydrous sodium sulfate and concentrated under reduced pressure. The residue was purified by silica gel column chromatography (Wako Gel C-200, 30 g; eluted with chloroform:methanol= 50:1) and further crystallized from diethyl ether to give the title compound (0.16 g, 0.53 mmol) as colorless crystals. (Yield starting from 3-cyano-5-hydroxypyridine 15%).

IR (KBr) cm$^{-1}$:3250, 2200, 1590.

FD-MS m/z 300 (M, C$_{15}$H$_{13}$N$_4$OCl).

$^1$H-NMR (90 MHz, CD$_3$OD): δ (ppm) 8.35(1H, d, J=1.8Hz, H-6), 8.22(1H, J=2.6Hz, H-2), 7.54(1H, dd, J=1.8, 2.6Hz , H-4) , 7.4-7.1(4H, C$_6$H$_4$Cl), 3.70(2H, m, NHC$\underline{H}_2$CH$_2$C$_6$H$_4$Cl), 3.08 (2H, t, J=7.3Hz, NHCH$_2$ C$\underline{H}_2$C$_6$H$_4$Cl).

Example 18

(Tablet/in 1 Tablet)

| | |
|---|---|
| 5-Amino-N-cyano-N'-[2-(2-chlorophenyl)ethyl]-3-pyridinecarboximidamide (N-cyano-N'-[2-(2-chlorophenyl)ethyl]-5-(3-aminopyridine)carboximidamide) | 2 mg |
| Lactose | 75.5 mg |
| Maize starch | 18 mg |
| Talc | 4 mg |
| Sodium stearate | 0.5 mg |
| Total | 100 (mg) |

The aforementioned ingredients are mixed and pressed into a tablet.

Example 19

(Capsule/in 1 Capsule)

| | |
|---|---|
| 5-Amino-N-cyano-N'-[2-(2-chlorophenyl)ethyl]-3-pyridinecarboximidamide (N-cyano-N'-[2-(2-chlorophenyl)ethyl]-5-(3-aminopyridine)carboximidamide) | 5 mg |
| Lactose | 94 mg |
| Sodium stearate | 1 mg |
| Total | 100 (mg) |

The aforementioned ingredients are mixed and capsuled to form a capsule.

(2) When $R^3$ in the formula (I) represents a nitroxyl group:
Pharmacological Test 1: Vasodilating effect in a rat aorta (1) Test Method Physiological effect of the compound of the present invention was tested by the method with use of an isolated rat aorta.

Thoracic aorta was isolated from a male Wistar rat (body weight, 250–350 g) exsanguinated to death for obtaining ring preparations having a width of 3 mm. The preparations were suspended into an organ bath filled with the Krebs-Ringer solution through which a mixed gas of 95% $O_2$ and 5% $CO_2$ had been aerated at 37° C. A resting tension of 1 g was applied to the preparation. After the tension in the preparation was stabilized, the solution in the organ bath was exchanged with an equimolar solution containing 40 mM KCl to increase the tension of the preparation. When the tension induced by KCl become stable, the test compound was cumulatively added to the organ bath to relax the preparation. Relaxation response was expressed as percentage inhibition of KCl-induced contraction, and the $IC_{50}$ value ( concentration for inhibiting 50% of the tension induced by KCl) was calculated from the average concentration-response curve by the Probit method.

(2) Results

The $IC_{50}$ values of the representative compounds among the compounds of the present invention are shown in Table 1.

TABLE 1

| Compound No. | $IC_{50}$ (M) |
|---|---|
| (18) | $2.2 \times 10^{-5}$ |
| (19) | $1.0 \times 10^{-5}$ |
| (20) | $2.7 \times 10^{-6}$ |
| (21) | $4.6 \times 10^{-6}$ |

Pharmacological Test 2: Antihypertensive Effects on SHR

Antihypertensive effects of- 5-amino-N-cyano-N'-( 2-nitroxyethyl)-3-pyridinecarboximidamide (N-cyano-N'-( 2-nitroxyethyl)-5-(3-aminopyridine)carboximidamide; Compound No. 18) and N-cyano-5-ethylamino-N'-(2-nitroxyethyl)-3-pyridinecarboximidamide (N-cyano-N'-(2-nitroxyethyl)-5-[3-(N-ethylaminopyridine)]carboximidamide; Compound No. 19) were assessed by comparison with those of the methanesulfonate salt of N-cyano-N'-(2-nitroxyethyl)-3-pyridinecarboximidamide (compound described in Japanese Patent Laid-Open Publication No. 163061/1991) as a reference compound which is thought to be a well-known compound most similar to the compound of the present invention.

(1) Test Method

Antihypertensive effects of the compound of the present invention were observed with conscious male spontaneously hypertensive rats (SHR). Systolic blood pressure (SBP) was measured with the tail cuff method.

Each of the compound Nos. 18 and 19 was dissolved in an equivalent mixture of polyethylene glycol 200 and physiological saline, and the reference compound was dissolved in physiological saline. The compounds were administered orally with the aid of an oral probe. SBP was measured before administration and 1, 2, 4, 6, 8, 12 and 24 hours after administration of the compound. The results were expressed as the percentage change in SBP observed before administration.

(2) Results

The decrease in blood pressure was observed on the administration of 3.0 mg/kg of Nos. 18 and 19. Antihypertensive effect induced by both drugs lasted for 12 hours or more (see Table 2). On the other hand, antihypertensive effect was also observed at the dose of 3.0 mg/kg of the reference compound but lasted for about 6 hours (see Table 2). Table 2: Antihypertensive effects of 5-amino-N-cyano-N'-( 2-nitroxyethyl)-3-pyridinecarboximidamide (Compound No. 18), N-cyano-5-ethylamino-N'-(2-nitroxyethyl)-3-pyridinecarboximidamide (Compound No. 19) and N-cyano-N'-( 2-nitroxyethyl)-3-pyridinecarboximidamide methanesulfonic acid (Reference Compound) on SHR (Data are expressed as the percent change in SBP observed before administration of the compound)

| | Time after administration (hour) | | | | | | |
|---|---|---|---|---|---|---|---|
| Compound No. | 1 | 2 | 4 | 6 | 8 | 12 | 24 |
| Reference Compound | −55.9 | −41.5 | −10.6 | −6.8 | | | |
| 18 | −56.9 | −49.2 | −42.6 | −17.9 | −20.5 | −22.2 | −3.7 |
| 19 | −60.2 | −47.2 | −24.3 | −23.9 | −25.9 | −27.7 | −9.8 |

Pharmacological Test 3: Coronary dilating effect of 5-amino-N-cyano-N'-(2-nitroxyethyl)- 3-pyridinecarboximidamide (Compound No. 18) on beagles Coronary dilating effects of 5-amino-N-cyano-N'-( 2-nitroxyethyl)-3-pyridinecarboximidamide (Compound No. 18) of the present invention was assessed by comparison with those of N-cyano-N'-(2-nitroxyethyl)-3-pyridinecarboximidamide methanesulfonic acid (compound described in Japanese Patent Laid-Open Publication No. 163061/1991) which is thought to be a well-known compound most similar to the compound of the present invention.

(1) Test Method

A dog (body weight, 8.3 kg) was anesthetized with 30 mg/kg of pentobarbital sodium intravenously. Respiration was maintained with room air through a cuffed endotracheal tube. The drug was administered through the femoral vein, and the coronary blood flow was measured by a probe attached to the circumflex branch of the left coronary artery.

(2) Results

When 5-amino-N-cyano-N'-(2-nitroxyethyl)-3-pyridinecarboximidamide (Compound No. 18) was administered intravenously in a dose of 10 Mg/Kg, and increase of coronary blood flow was observed and retained for 15 minutes or more. While the increase in coronary blood flow was observed with N-cyano-N'-(2-nitroxyethyl) 3-pyridinecarboximidamide methanesulfonic acid (Reference Compound) in a dose of 10 Mg/Kg, it was retained only 10 minutes or less. Table 3: Effects of 5-amino-N-cyano-N'-(2-nitroxyethyl)- 3-pyridinecarboximidamide (Compound No. 18) and N-cyano-N'-( 2-nitroxyethyl)-3-pyridinecarboximidamide methanesulfonic acid (Reference Compound) administered intravenously in a dose of 10 Mg/Kg on coronary blood flow (anesthetized dog) (Data are expressed as percent change as compared with the blood flow before administration of the compound)

|  | Time after dosage (min) | | | | | |
| --- | --- | --- | --- | --- | --- | --- |
| Compound No. | 1 | 3 | 5 | 10 | 15 | 20 |
| 18 | 200.0 | 123.8 | 71.4 | 19.0 | 19.0 | 0.0 |
| Reference compound | 219.0 | 42.9 | 14.3 | 0.0 | | |

Pharmacological Test 4: Acute Toxicity

Acute toxicity of 5-amino-N-cyano-N'-(2-nitroxyethyl)-3-pyridinecarboximidamide (Compound No. 18) of the present invention on oral administration was examined with male SD rats (5 weeks old). As a result, $LD_{50}$ was about 600 mg/kg.

Example 1 Preparation of 5-amino-N-cyano-N'-(2-nitroxyethyl)-3-pyridinecarboximidamide To a solution of 2-nitroxyethylamine hydrochloride (140 mg, 0.98 mmol) in DMF (1 ml) was added sodium methoxide (42 mg, 0.78 mmol) followed by a solution of propyl 5-amino-N-cyano-3-pyridinecarboximidate (100 mg, 0.49 mmol) in methanol (1 ml) described in Example 6 of Experimental Example 1, and the mixture was stirred at room temperature for 3 hours. After the reaction was completed, the reaction mixture was evaporated under reduced pressure. The residue was suspended in water and extracted with chloroform. The chloroform layer was dried over anhydrous sodium sulfate and concentrated under reduced pressure. The residue thus obtained was purified by silica gel column chromatography with a mixed solvent of methanol and chloroform as an eluent to give the title compound (77 mg, yield 63%) as colorless crystals.

Mp 121° C.

IR (KBr) cm$^{-1}$:3230, 2160, 1640, 1570, 1280.

$^1$H-NMR (90 MHz, CD$_3$OD): δ (ppm) 8.12(1H, d, J=2.6Hz), 7.93(1H, d, J=2.0Hz), 7.24(1H, dd, J=2.6, 2.0Hz), 4.74(2H, t, J=5.2Hz), 3.80(2H, t, J=5.2Hz).

MS 250 (M+), 188 [(M-ONO$_2$)$^+$].

Example 2

Preparation of N-cyano-5-ethylamino-N'-(2-nitroxyethyl)-3-pyridinecarboximidamide To a solution of 2-nitroxyethylamine hydrochloride (659 mg, 4.62 mmol) in DMF (1 ml) was added sodium methoxide (227 mg, 4.20 mmol) followed by a solution of propyl N-cyano-5-ethylamino-3-pyridinecarboximidate (195 mg, 0.84 mmol) in DMF (1 ml) described in Example 10 of Experimental Example 1, and the mixture was stirred at room temperature for 3 hours. After the reaction was completed, the reaction mixture was evaporated under reduced pressure. The residue was suspended in water and extracted with chloroform. The chloroform layer was dried over anhydrous sodium sulfate and concentrated under redeuced pressure. The residue thus obtained was purified by silica gel column chromatography with a mixed solvent of methanol and chloroform as an eluent to give the title compound (208 mg, yield 89%) as colorless crystals.

Mp 100° C.

IR (KBr) cm$^{-1}$:3230, 2170, 1630, 1550, 1275.

$^1$H-NMR (90 MHz, CDC13): δ (ppm) 8.28(1H, brt), 7.97(1H, d, J=2.6Hz), 7.89(1H, J=1.8Hz), 7.12(1H, dd, J=2.6, 1.8Hz), 4.70(2H, t, J=5.0Hz), 3.83(2H, m), 3.15(2H, m), 1.25(3H, t, J=7.2Hz).

MS 278 (M$^+$), 216 [(M-ONO$_2$)$^+$].

Example 3

Preparation of 6-amino-N-cyano-N'-(2-nitroxyethyl)-3-pyridinecarboximidamide

To a solution of 2-nitroxyethylamine hydrochloride (1.36 g, 9.54 mmol) in DMF (3.5 ml) was added sodium methoxide (470 mg, 8.7 mmol) followed by a solution of propyl N-cyano-6-amino-3-pyridinecarboximidate (355 mg, 1.74 mmol) in DMF (2 ml) described in Example 5 of Experimental Example 1, and the mixture was stirred at room temperature for 3 hours. After the reaction was completed, the reaction mixture was evaporated under reduced pressure. The residue was suspended in water and extracted with chloroform. The chloroform layer was dried over anhydrous sodium sulfate and concentrated under reduced pressure. The residue thus obtained was purified by silica gel column chromatography with a mixed solvent of methanol and chloroform as an eluent to give the title compound (284 mg, yield 74%) as colorless crystals.

Mp 108° C.

IR (KBr) cm$^{-1}$:3230, 2160, 1640, 1570, 1280.

$^1$H-NMR (90 MHz, DMSO): δ (ppm) 9.00(1H, brt), 8.23(1H, dd, J=2.42, 0.66Hz), 7.66(1H, dd, J=8.79,-2.64Hz), 6.72(2H, brs), 6.50(1H, dd, J=8.79, 0.88Hz), 4.70(2H, t, J=5.27Hz), 3.66(2H, m).

MS 250 (M$^+$), 188 [(M-ONO$_2$)$^+$].

Example 4

Preparation of N-cyano-6-diethylamino-N'-(2-nitroxyethyl),3-pyridinecarboximidamide To a solution of 6-chloro-3-cyanopyridine (500 mg, 3.60 mmol) in DMF (5 ml) were added potassium carbonate (500 mg, 3.62 mmol), sodium iodide (catalytic amount) and diethylamine (400 mg, 5.50 mmol), and the mixture was stirred at 120° C. for 3 hours. The reaction mixture, to which water (5 ml) was added, was extracted with ethyl acetate. The ethyl acetate layer was washed with a saturated brine, dried over anhydrous sodium sulfate and concentrated under reduced pressure. The residue thus obtained was purified by silica gel column chromatography with a mixed solvent of ethyl acetate and hexane as an eluent to give the title compound (560 mg, yield 89%) as white crystals.

IR (neat) cm$^{-}$:2200, 1600, 1540, 1510.

$^1$H-NMR (90 MHz, CDCl$_3$): δ (ppm) 8.39(1H, d, J=2.44Hz), 7.55(1H, dd, J=9.16, 2.44Hz), 6.45(1H, d, J=9.16Hz), 3.55(4H, q, J=7.30Hz), 1.20(6H, t, J=7.30Hz).

Into a solution of 6-diethylamino-3-cyanopyridine (460 mg, 2.63 mmol) in 1-propanol (15 ml) was passed hydrogen chloride gas at a temperature of 0°–5° C. for 30 minutes. The reactor was tight sealed, and the mixture was stirred at 0° C. over night. After the reaction was completed, the reaction mixture was concentrated under reduced pressure, and the residue was added to a concentrated sodium carbonate solution. After it was confirmed that the solution showed an alkaline pH (9 or more), it was extracted with chloroform. The chloroform layer was dried over anhydrous sodium sulfate and concentrated under reduced pressure to give a crude product of propyl 6-diethylamino-3-pyridinecarboximidate as an oil. The oil was dissolved in acetonitrile (2 ml), and an aqueous solution (5 ml) of NaH$_2$PO$_4$·2H$_2$O (1.62 g, 10.4 mmol), Na$_2$HPO$_4$ (370 mg, 2.61 mmol) and cyanamide (220 mg, 5.24 mmol) was added to the solution. The mixture was stirred at room temperature over night. After the reaction was completed, the reaction mixture was extracted with chloroform, and the chloroform layer was dried over anhydrous sodium sulfate and concentrated under reduced pressure. The residue obtained was purified by silica gel column chromatography with a mixed solvent of methanol and chloroform to give propyl N-cyano- 6-diethylamino-3-pyridinecarboximidate (630 mg, yield 92%) as a colorless oil.

IR (neat) cm$^{-1}$:2960, 2180, 1580, 1280.

$^1$H-NMR (500 MHZ, CDCl$_3$): δ (ppm) 8.90(1H, d, J=2.45Hz), 8.38(1H, d, J=2.44Hz), 7.55(1H, dd, J=9.16, 2.44Hz), 6.47(1H, d, J=9.16Hz), 4.31(2H, t, J=6.41Hz), 3.59(4H, q, J=7.33Hz), 1.81(2H, m), 1.22 (6H, t, J=7.33Hz), 1.03 (3H, t, J=7.21Hz).

To a solution of 2-nitroxyethylamine hydrochloride (314 mg, 2.20 mmol) in methanol (3 ml) was added sodium methoxide (115 mg, 2.13 mmol) followed by a solution of propyl N-cyano-6-diethylamino-3-pyridinecarboximidate (370 mg, 1.42 mmol) in methanol (2 ml), and the mixture was stirred at room temperature for 5 hours. After the reaction was completed, the reaction mixture was concentrated to dryness under reduced pressure. The residue was suspended in water and extracted with ethyl acetate. The ethyl acetate layer was washed with a saturated saline solution, dried over anhydrous sodium sulfate and concentrated under reduced pressure. The residue thus obtained was purified by silica gel column chromatography with a mixed solvent of ethyl acetate and hexane as an eluent to give the title compound (183 mg, yield 42%) as colorless crystals.

Mp 119° C.

IR (KBr) cm$^{-1}$:2160, 1635, 1565, 1275.

$^1$H-NMR (500 MHz, CDCl$_3$): δ (ppm) 8. 41(1H, d, J=3.05Hz), 7.84(1H, dd, J=9.15, 3.05Hz), 6.52(1H, brs), 6.50(1H, d, J=9.15Hz), 4.68(2H, t, J=5.18Hz), 3.82(2H, m), 3.55(4H, q, J=7.32Hz), 1.20(6H, t, J=7.33Hz).

MS 306 (M$^+$), 244 [(M-ONO$_2$)$^+$].

Example 5

Preparation of 5-N-Butylamino-N-Cyano-N'-(2-nitroxyethyl)-3pyridinecarboximidamide To a solution of 2-nitroxyethylamine hydrochloride (443 mg, 3.11 mmol) in DMF (2 ml) was added sodium methoxide (153 mg, 2.83 mmol)-followed by a solution of propyl 5-n-butylamino-N-cyano-3-pyridinecarboximidate (147 mg, 0.56 mmol) described in Example 12 of Experimental Example 1 in DMF (1 ml), and the mixture was stirred at room temperature for 4 hours. After the reaction was completed, the reaction mixture was concentrated to dryness under reduced pressure. The residue was suspended in water and extracted with chloroform. The chloroform layer was dried over anhydrous sodium sulfate and concentrated under reduced pressure. The residue thus obtained was purified by silica gel column chromatography with a mixed solvent of methanol and chloroform as an eluent to give the title compound (145 mg, yield 83%) as colorless crystals.

Mp 103.5° C.

IR (KBr) cm$^{-1}$:3230, 2170, 1630, 1580, 1555, 1275.

$^1$H-NMR (90 MHz, CDCl$_3$): δ (ppm) 8.01(1H, d, J=2.6Hz), 7.91(1H, d, J=1.8Hz), 7.80(1H, brt), 7.15(1H, dd, J=2.6, 1.8Hz), 4.71(2H, t, J=5.1Hz), 4.49(1H, brs), 3.82(2H, m), 3.12(2H, m), 1.8-1.2(4H, m), 0.96(3H, t, J=6.37).

MS 306 (M$^+$), 244 [(M-ONO$_2$)$^+$].

Example 6

Preparation of N-Cyano-N'-(2-nitroxyethyl)-5-isopropylamino-3-pyridinecarboximidamide To a solution of 2-nitroxyethylamine hydrochloride (95 mg, 0.67 mmol) in DMF (1 ml) was added sodium methoxide (25 mg, 0.46 mmol) followed by a solution of propyl N-cyano-5-isopropylamino-3-pyridinecarboximidate (80 mg, 0.33 mmol) described in Example 11 of Experimental Example 1 in DMF (1 ml), and the mixture was stirred at room temperature for 3 hours. After the reaction was completed, the reaction mixture was concentrated to dryness under reduced pressure. The residue was suspended in water and extracted with chloroform. The chloroform layer was dried over anhydrous sodium sulfate and concentrated under reduced pressure. The residue thus obtained was purified by silica gel column chromatography with a mixed solvent of methanol and chloroform as an eluent to give the title compound (26 mg, yield 27%) as colorless crystals.

Mp 123° C.

IR (KBr) cm$^{-1}$:3220, 2200, 1640, 1590, 1560, 1280, 1000, 845.

$^1$H-NMR (90 MHz, CDCl$_3$-CD$_3$OD): δ (ppm) 7.97(1H, d, J=3.9Hz), 7.86(1H, d, J=1.5Hz), 7.03(1H, dd, J=3.9, 1.5Hz), 4.62(2H, t, J=5.0Hz), 3.80(1H, m), 3.57(1H, m), 1.25(6H, d, J=6.4Hz).

MS 292 (M$^+$), 230 [(M-ONO$^2$)$^+$].

Example 7

Preparation of 5-acetylamino-N-cyano-N'-(2-nitroxyethyl)-3-pyridinecarboximidamide To a solution of 5-amino-N-cyano-N'-(2-nitroxyethyl)-3-pyridinecarboximidamide (105 mg, 0.42 mmol) (see Example 1) in pyridine (1 ml) was added acetyl chloride (45 μl, 0.63 mmol), and the mixture was reacted at room temperature for 1 hour. After the reaction was completed, a cold aqueous sodium hydrogen carbonate solution was added, and the mixture was extracted with ethyl acetate. The ethyl acetate layer was washed with brine, dried over anhydrous sodium sulfate and concentrated under reduced pressure. The residue thus obtained was purified by silica gel column chromatography with a mixed solvent of methanol and chloroform as an eluent to give the title compound (116 mg, yield 95%) as hygroscopic powder.

IR (KBr) cm$^{-1}$:2180, 1680, 1635, 1565, 1450, 1280.

$^1$H-NMR (90 MHz, CDCl$_3$): δ (ppm) 10.5(1H, brs), 9.54(1H, brt), 8.90(1H, d, J=2.4Hz), 8.42(1H, d, J=2.0Hz), 8.27(1H, dd, J=2.4, 2.0Hz), 4.75(2H, t, J=5.1Hz), 3.73(2H, m), 3.31(3H, s).

MS 292 (M$^+$), 230 [(M-ONO$_2$)$^+$].

Example 8

(Tablet/in 1 tablet)

| | |
|---|---|
| 5-amino-N-cyano-N'-(2-nitroxyethyl)-3-pyridinecarboximidamide | 2 mg |
| Lactose | 75.5 mg |
| Maize starch | 18 mg |
| Talc | 4 mg |
| Magnesium stearate | 0.5 mg |
| Total | 100 mg |

The aforementioned ingredients are mixed together and pressed into a tablet.

Example 9

(Capsule/in 1 capsule)

| | |
|---|---|
| 5-amino-N-cyano-N'-(2-nitroxyethyl)-3-pyridinecarboximidamide | 5 mg |
| Lactose | 94 mg |
| Magnesium stearate | 1 mg |
| Total | 100 mg |

The aforementioned ingredients are mixed together and capsulated to form a capsule.

Example 10

(Injection/in 1 vial)

| | |
|---|---|
| 5-amino-N-cyano-N'-(2-nitroxyethyl)-3-pyridinecarboximidamide | 1 mg |
| Maltose | 25 mg |
| Distilled water for injection | as required |
| Total | 2 ml |

The aforementioned ingredients are mixed together, filtered and filled into a vial. After lyophilization, the vial is tight sealed for injection.

Industrial Applicability

The compounds according to the present invention have vasodilating effect, more specifically, hypotensive activity or antianginal effect, which are thus useful as antihypertensive agents or antianginal agents.

We claim:

1. A pyridinecarboximidamide represented by the formula (I):

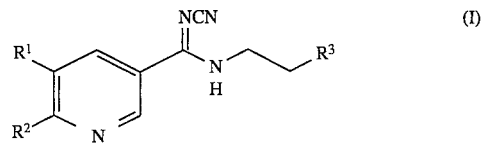

wherein

R$^1$ is selected from a hydroxyalkyl, carboxyl, amino, acylamino, alkylamino, dialkylamino, aralkylamino, alkylsulfonamide, bisalkylsulfonylamino or hydroxyl group, R$^2$ represents a hydrogen atom and R$^3$ represents a nitroxyl, 2-chlorophenyl or phenyl group, or R$^1$ represents a hydrogen atom, R$^2$ represents a hydroxyalkyl, carboxyl, amino, acylamino, alkylamino, dialkylamino, aralkylamino, alkylsulfonamide, bisalkylsulfonylamino or hydroxyl group and R$^3$ represents a nitroxyl, 2-chlorophenyl or phenyl group; or an acid adduct salt thereof.

2. A pyridinecarboximidamide or an acid adduct salt thereof according to claim 1, which is a compound represented by the formula (I-a):

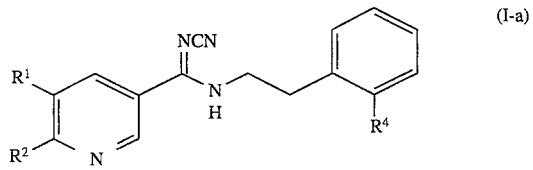

wherein

R$^1$ is selected from a hydroxyalkyl, carboxyl, amino, acylamino, alkylamino, dialkylamino, aralkylamino, alkylsulfonamide, bisalkylsulfonylamino or hydroxyl group, R$^2$ represents a hydrogen atom and R$^4$ represents a hydrogen or chlorine atom, or R$^1$ represents a hydrogen atom, R$^2$ represents a hydroxyalkyl, carboxyl, amino, acylamino, alkylamino, dialkylamino, aralkylamino, alkylsulfonamide, bisalkylsulfonylamino or hydroxyl group and R$^4$ represents a hydrogen or chlorine atom.

3. A pyridinecarboximidamide or an acid adduct salt thereof according to claim 1, which is a compound represented by the formula (I-b):

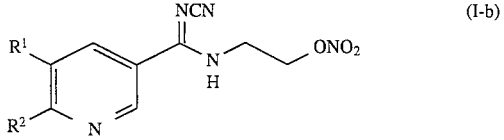

wherein

R$^1$ is selected from a hydroxyalkyl, carboxyl, amino, acylamino, alkylamino, dialkylamino, aralkylamino, alkylsulfonamide, bisalkylsulfonylamino or hydroxyl group, $R^2$ represents a hydrogen atom, or when $R^1$ represents a hydrogen atom, $R^2$ represents a hydroxyalkyl, carboxyl, amino, acylamino, alkylamino, dialkylamino, aralkylamino, alkylsulfonamide, bisalkylsulfonylamino or hydroxyl group.

4. A pyridinecarboximidamide or an acid adduct salt thereof according to claim 1, wherein, as $R^1$ and $R^2$ in the formula (I) [are such that the alkyl group has 1 to 5 carbon atoms,] alkyl of the hydroxyalkyl group has 1 to 5 carbon atoms, acyl of the acylamino group is acetyl, propionyl or benzoyl, alkyl of the alkylamino group has 1 to 5 carbon atoms, alkyl of the dialkylamino group has 1 to 5 carbon atoms, the aralkylamino group is benzylamino, alkyl of the alkylsulfonamide group has 1 to 5 carbon atoms, and alkyl of the bisalkylsulfonylamino group has 1 to 5 carbon atoms.

5. A pyridinecarboximidamide or an acid adduct salt adduct thereof according to claim 2, wherein $R^1$ and $R^2$ in the formula (I-a) [are such that the alkyl group has 1 to 5 carbon atoms,] alkyl of the hydroxyalkyl group has 1 to 5 carbon atoms, acyl of the acylamino group is acetyl, propionyl or benzoyl, alkyl of the alkylamino group has 1 to 5 carbon atoms, alkyl of the dialkylamino group has 1 to 5 carbon atoms, the aralkylamino group is benzylamino, alkyl of the alkylsulfonamide group has 1 to 5 carbon atoms, and alkyl of the bisalkylsulfonylamino group has 1 to 5 carbon atoms.

6. A pyridinecarboximidamide or an acid adduct salt adduct thereof according to claim 3, wherein $R^1$ and $R^2$ in the formula (I-b) [are such that the alkyl group has 1 to 5 carbon atoms,] alkyl of the hydroxyalkyl group has 1 to 5 carbon atoms, acyl of the acylamino group is acetyl, propionyl or benzoyl, alkyl of the alkylamino group has 1 to 5 carbon atoms, alkyl of the dialkylamino group has 1 to 5 carbon atoms, the aralkylamino group is benzylamino, alkyl of the alkylsulfonamide group has 1 to 5 carbon atoms, and alkyl of the bisalkylsulfonylamino group has 1 to 5 carbon atoms.

7. A pyridinecarboximidamide or an acid adduct salt adduct thereof according to claim 5, which is selected from the group consisting of the following compounds or an acid adduct salt thereof:

1) N-cyano-N'-[2-(2-chlorophenyl)ethyl]-5-hydroxymethyl-3-pyridinecarboximidamide, 2) 5-carboxy-N-cyano-N'-[2-(2-chlorophenyl) ethyl]-3-pyridinecarboximidamide, 3) 6-amino-N-cyano-N'-[2-(2-chlorophenyl)ethyl]- 3-pyridinecarboximidamide, 4) 5-amino-N-cyano-N'-[2-(2chlorophenyl)ethyl]-3-pyridinecarboximidamide, 5) 5-acetamide-N-cyano-N'-[2-(2chlorophenyl)ethyl]-3-pyridinecarboximidamide, 6) 5-benzamide-N-cyano-N'-[2-(2chlorophenyl)ethyl]-3-pyridinecarboximidamide, 7) N-cyano-N'-[2-(2-chlorophenyl)ethyl]-5-dimethylamino-3-pyridinecarboximidamide, 8) N-cyano-N'-[2-(2-chlorophenyl)ethyl]-5-ethylamino-3-pyridinecarboximidamide, 9) N-cyano-N'-[2-(2-chlorophenyl)ethyl]-5-isopropylamino-3-pyridinecarboximidamide, 10) 5-n-butylamino-N-cyano-N'-[2-(2chlorophenyl)ethyl]-3-pyridinecarboximidamide, 11) 5-benzylamino-N-cyano-N'-[2-(2chlorophenyl)ethyl]-3-pyridinecarboximidamide, 12) N-cyano-N'-[2-(2-chlorophenyl)ethyl]-5-methanesulfonamide-3-pyridinecarboximidamide, 13) N-cyano-N'-[2-(2-chlorophenyl)ethyl]-5-bismethanesulfonylamino-3-pyridinecarboximidamide, 14) 5-amino-N-cyano-N'-(2-phenethyl)-3-pyridinecarboximidamide, and 15) N-cyano-N'-[2-(2-chlorophenyl)ethyl]- 5-hydroxy-3-pyridinecarboximidamide.

8. A pyridinecarboximidamide or an acid adduct salt thereof according to claim 6, which is selected from the group consisting of the following compounds or an acid adduct salt thereof:

1) 5-amino-N-cyano-N'-(2-nitroxyethyl)-3-pyridinecarboximidamide,

2) N-cyano-5-ethylamino-N'-(2-nitroxyethyl)-3-pyridinecarboximidamide, 3) 6-amino-N-cyano-N'-(2-nitroxyethyl)-3-pyridinecarboximidamide, 4) N-cyano-6-diethylamino-N'-(2-nitroxyethyl)- 3-pyridinecarboximidamide, 5) 5-n-butylamino-N-cyano-N'-(2-nitroxyethyl)- 3-pyridinecarboximidamide, 6) N-cyano-N'-(2-nitroxyethyl)-5-isopropylamino- 3-pyridinecarboximidamide, and 7) 5-acetylamino-N-cyano-N'-(2-nitroxyethyl)- 3-pyridinecarboximidamide.

9. A pyridinecarboximidamide or an acid adduct salt thereof according to claim 5, which is the following compound or an acid adduct salt thereof:

5-amino-N-cyano-N'-[2-(2-chlorophenyl)ethyl]- 3-pyridinecarboximidamide.

10. A pyridinecarboximidamide or an acid adduct salt thereof according to claim 6, which is the following compound or an acid adduct salt thereof:

5-amino-N-cyano-N'-(2-nitroxyethyl)-3-pyridinecarboximidamide.

11. A pharmaceutical composition useful for treating hypertension comprising a pyridinecarboximidamide represented by the formula (I-a) or an acid adduct salt thereof as set forth in any one of claims 2, 5 and 7, together with a pharmaceutically acceptable carrier.

12. A pharmaceutical composition according to claim 11, wherein the pyridinecarboximidamide or an acid adduct salt thereof is the following compound: 5-amino-N-cyano-N'-[2-(2chlorophenyl)ethyl]- 3-pyridine-carboximidamide.

13. A pharmaceutical composition useful for treating hypertension comprising a pyridinecarboximidamide represented by the formula (I-b) or an acid adduct salt thereof as set forth in any one of claims 3, 6 and 8, together with a pharmaceutically acceptable carrier.

14. A pharmaceutical composition according to claim 13, wherein the pyridinecarboximidamide or an acid adduct salt thereof is the following compound: 5-amino-N-cyano-N'-( 2-nitroxyethyl)-3-pyridine-carboximidamide.

15. A pharmaceutical composition useful for treating angina pectoris comprising a pyridinecarboximidamide represented by the formula (I-b) or an acid adduct salt thereof as set forth in any one of claims 3, 6 and 8, together with a pharmaceutically acceptable carrier.

16. A pharmaceutical composition according to claim 15, wherein the pyridinecarboximidamide or an acid adduct salt thereof is the following compound: 5-amino-N-cyano-N'-(2-nitroxyethyl)- 3-pyridine-carboximidamide.

17. A method for the treatment of hypertension, wherein a pyridinecarboximidamide represented by the formula (I-a) or an acid adduct salt thereof as set forth in any one of claims 2, 5 and 7 is administered to a patient who needs the treatment of hypertension.

18. A method for the treatment of hypertension according to claim 17, wherein the pyridinecarboximidamide or an acid adduct salt thereof is the following compound:

5-amino-N-cyano-N'-[2-(2-chlorophenyl)ethyl]-3-pyridinecarboximidamide.

19. A method for the treatment of hypertension wherein a pyridinecarboximidamide represented by the formula (I-b) or an acid adduct salt thereof as set forth in any one of claims 3, 6 and 8 is administered to a patient who needs the treatment of hypertension.

20. A method for the treatment of hypertension according to claim 19, wherein the pyridinecarboximidamide or an acid adduct salt thereof is the following compound: 5-amino-N-cyano-N'-(2-nitroxyethyl)-3-pyridinecarboximidamide.

21. A method for the treatment of angina pectoris, wherein a pyridinecarboximidamide represented by the formula (I-b) or an acid adduct salt thereof as set forth in any one of claims 3, 6 and 8 is administered to a patient of angina pectoris.

22. A method for the treatment of angina pectoris according to claim 21, wherein the pyridinecarboximidamide or an acid adduct salt thereof is the following compound:

5-amino-N-cyano-N'-(2-nitroxyethyl)-3-pyridinecarboximidamide.

23. A pyridinecarboximidamide represented by the formula (I)

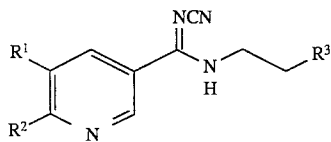

wherein

R$^1$ is selected from a hydroxyalkyl, amino, acylamino or alkylamino group, R$^2$ represents a hydrogen atom, and R$^3$ represents a nitroxyl, 2-chlorophenyl or phenyl group, or R$^1$ represents a hydrogen atom, R$^2$ represents a hydroxyalkyl, amino, acylamino or alkylamino group, and R$^3$ represents a nitroxyl, 2-chlorophenyl or phenyl group; or an acid adduct salt thereof.

24. A pyridinecarboximidamide or an acid adduct salt thereof according to claim 23, which is a compound represented by the formula (I-a):

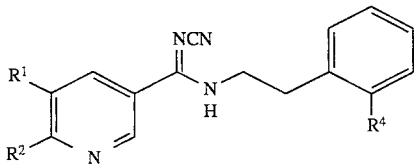

wherein

R$^1$ is selected from a hydroxyalkyl, amino, acylamino or alkylamino group, R$^2$ represents a hydrogen atom and R$^4$ represents a hydrogen or chlorine atom, or R$^1$ represents a hydrogen atom, R$^2$ represents hydroxyalkyl, amino, acylamino or alkylamino group and R$^4$ represents a hydrogen or chlorine atom.

25. A pyridinecarboximidamide or an acid adduct salt thereof according to claim 23, which is a compound represented by the formula (I-b):

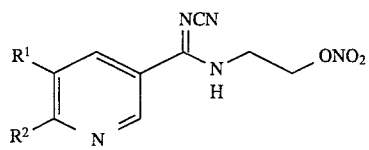

wherein

R$^1$ is selected from a hydroxyalkyl, amino, acylamino or alkylamino group, R$^2$ represents a hydrogen atom, or R$^1$ represents a hydrogen atom, R$^2$ represents a hydroxyalkyl, amino, acylamino or alkylamino group.

26. A pyridinecarboximidamide or an acid adduct salt thereof according to claim 23, wherein, R$^1$ and R$^2$ in the formula (I), alkyl of the hydroxyalkyl group has 1 to 5 carbon atoms, acyl of the acylamino group is acetyl, propionyl or benzoyl and alkyl of the alkylamino group has 1 to 5 carbon atoms.

27. A pyridinecarboximidamide or an acid adduct salt thereof according to claim 24, wherein, R$^1$ and R$^2$ in the formula (I-a), alkyl of the hydroxyalkyl group has 1 to 5 carbon atoms, acyl of the acylamino group is acetyl, propionyl or benzoyl and alkyl of the alkylamino group has 1 to 5 carbon atoms.

28. A pyridinecarboximidamide or an acid adduct salt thereof according to claim 25, wherein, R$^1$ and R$^2$ in the formula (I-b), alkyl of the hydroxyalkyl group has 1 to 5 carbon atoms, acyl of the acylamino group is acetyl, propionyl or benzoyl and alkyl of-the alkylamino group has 1 to 5 carbon atoms.

29. A pyridinecarboximidamide or an acid adduct salt thereof according to claim 27, which is selected from the group consisting of the following compounds or an acid adduct salt thereof:

1) N-cyano-N'-[2-(2-chlorophenyl)ethyl]-5-hydroxymethyl-3-pyridinecarboximidamide, 2) 6-amino-N-cyano-N'-[2-(2-chlorophenyl)ethyl)-3-pyridinecarboximidamide, 3) 5-amino-N-cyano-N'-[2-(2-chlorophenyl)ethyl]-3-pyridinecarboximidamide, 4) 5-acetamide-N-cyano-N'-[2-(2-chlorophenyl)]3-pyridinecarboximidamide, 5) N-cyano-N'-[2-(2-chlorophenyl)ethyl)-5-ethylamino-3-pyridinecarboximidamide, 6) N-cyano-N'-[2-(2-chlorophenyl)ethyl)-5-isopropylamino-3-pyridinecarboximidamide, 7) 5-n-butylamino-N-cyano-N'-[2-(2chlorophenyl)ethyl]-3-pyridinecarboximidamide, and 8) 5-amino-N-cyano-N'-(2-phenethyl)-3-pyridinecarboximidamide.

30. A pyridinecarboximidamide or an acid adduct salt thereof according to claim 28, which is selected from the group consisting of the following compounds or an acid adduct salt thereof:

1) 5-amino-N-cyano-N'-(2-nitroxyethyl)-3-pyridinecarboximidamide,

2) N-cyano-5-ethylamino-N'-(2-nitroxyethyl)-3-pyridinecarboximidamide, 3) 6-amino-N-cyano-N'-(2-nitroxyethyl)-3-pyridinecarboximidamide, 4) 5-n-butylamino-N-cyano-N'-(2-nitroxyethyl)-3-pyridinecarboximidamide, 5) N-cyano-N'-(2-nitroxyethyl)-5-isopropylamino-3-pyridinecarboximidamide, and 6) 5-acetylamino-N-cyano-N'-(2-nitroxyethyl)-3-pyridinecarboximidamide.

* * * * *

UNITED STATES PATENT AND TRADEMARK OFFICE
CERTIFICATE OF CORRECTION

PATENT NO. : 5,508,293
DATED      : April 16, 1996
INVENTOR(S): Hideki OKAWARA, et al.

It is certified that error appears in the above-indentified patent and that said Letters Patent is hereby corrected as shown below:

On the title page, Item [54], and Col. 1, lines 1-2, the title, should read:

--PYRIDINECARBOXIMIDAMIDE COMPOUNDS AND THE
  USE THEREOF--

Signed and Sealed this

Twenty-third Day of July, 1996

*Attest:*

BRUCE LEHMAN

*Attesting Officer*    Commissioner of Patents and Trademarks

UNITED STATES PATENT AND TRADEMARK OFFICE
CERTIFICATE OF CORRECTION

PATENT NO. : 5,508,293

DATED : April 16, 1996

INVENTOR(S) : Hideki OKAWARA, et al.

It is certified that error appears in the above-identified patent and that said Letters Patent is hereby corrected as shown below:

Column 29, line 24, "Mg/Kg" should read --µg/kg--;
 line 29, "Mg/Kg" should read --µg/kg--;
 line 34, "Mg/Kg" should read --µg/kg--.

Signed and Sealed this

Twenty-eighth Day of April, 1998

*Attest:*

BRUCE LEHMAN

*Attesting Officer*     *Commissioner of Patents and Trademarks*